(12) United States Patent
Yamasaki et al.

(10) Patent No.: US 7,087,747 B2
(45) Date of Patent: Aug. 8, 2006

(54) µ-OXO BRIDGED HETEROMETAL COMPOUND AND SELECTIVE PRODUCTION METHOD THEREOF

(75) Inventors: Yasuhiro Yamasaki, Neyagawa (JP); Kenji Takaki, Yawata (JP)

(73) Assignee: Orient Chemical Industries, Ltd., Osaka-fu (JP)

( * ) Notice: Subject to any disclaimer, the term of this patent is extended or adjusted under 35 U.S.C. 154(b) by 185 days.

(21) Appl. No.: 10/701,610

(22) Filed: Nov. 6, 2003

(65) Prior Publication Data

US 2004/0091742 A1 May 13, 2004

(30) Foreign Application Priority Data

Nov. 8, 2002 (JP) .................................. 2002-325347

(51) Int. Cl.
*C09B 47/04* (2006.01)
*C07D 487/22* (2006.01)

(52) U.S. Cl. ................. 540/139; 540/123; 540/125; 540/128; 540/140; 540/141

(58) Field of Classification Search ............. 540/139, 540/123, 125, 128, 140, 141
See application file for complete search history.

(56) References Cited

U.S. PATENT DOCUMENTS 4,719,613 A  1/1988  Hirose et al.
4,900,817 A  2/1990  Batzel et al.
5,039,798 A  8/1991  Johnson
5,213,929 A * 5/1993  Takano et al. ................. 430/78
2003/0082469 A1  5/2003  Tamura

FOREIGN PATENT DOCUMENTS

| DE | 4231762 A1 | | 3/1994 |
|---|---|---|---|
| EP | 0798346 A2 | * | 10/1997 |
| EP | 1004634 A2 | * | 5/2000 |
| JP | 2-73871 A | | 3/1990 |
| JP | 4-184452 A | | 7/1992 |
| WO | WO01/50199 A1 | | 7/2001 |

OTHER PUBLICATIONS

English language abstract of JP 04 351673 A (Dec. 7, 1992).

* cited by examiner

*Primary Examiner*—Richard L. Raymond
*Assistant Examiner*—Paul V. Ward
(74) *Attorney, Agent, or Firm*—Birch, Stewart, Kolasch & Birch, LLP

(57) ABSTRACT

An object of the present invention is to provide a new µ-oxo bridged heterometal compound, which can make the photo-functional materials to have diversified properties, and a production method such that the µ-oxo bridged heterometal compound is obtained simply, selectively and with high yield. The present invention provides µ-oxo bridged heterometal compounds, NcM1-O-M2Nc, PcM1-O-M2Nc and NcM1-O-M2Pc wherein Nc represents naphthalocyanine, Pc represents phthalocyanine, M1 represents a metal atom which is able to have a valence of up to three, and M2 represents a metal atom which is able to have a valence of four or five.

9 Claims, 11 Drawing Sheets

μ-OXO BRIDGED HETEROMETAL COMPOUND AND SELECTIVE PRODUCTION METHOD THEREOF

This Nonprovisional application claims priority under 35 U.S.C. § 119(a) on Patent Application No(s). 2002-325347 filed in JAPAN on Nov. 8, 2002, the entire contents of which are hereby incorporated by reference.

BACKGROUND OF THE INVENTION

1. Field of the Invention

The present invention relates to a new μ-oxo bridged heterometal naphthalo/naphthalocyanine compound which is useful for electric charge generating materials such as organic photoreceptors, photoconductive materials, optical recording materials, organic solar cell materials, nonlinear optical materials and the like, and to a production method thereof.

2. Description of the Related Art

Phthalocyanine-based compounds or naphthalocyanine-based compounds have been noted as organic photoconductive substances having sensitivity around a wavelength of 800 nm which is an oscillation wavelength range of a semiconductor laser. A number of organic photoreceptors (OPC) including such organic photoconductive substances as effective components have been proposed. For example, organic photoreceptors employing titanylphthalocyanine-based compounds as electric charge generating materials have been made to practical use.

Recently, medium-to-high sensitive electric charge generating materials provided with a new performance, that are suitable for the shortwaving of a light source by the prevalence of light-emitting diodes (LED) and OPC for color laser-beam printers (LBP), have been vigorously searched.

It has been known that phthalocyanine (Pc) compounds generate electric charge by irradiating and offer diverse electrical properties in accordance with polymorphs thereof, presence or absence, and kind of central metal thereof, and the like.

For example, with regard to a mixed crystal of two or more kinds of phthalocyanine compounds, Japanese Patent Laid-Open Publication No. H2(1990) 272067 discloses a production method of an X-type metal-free phthalocyanine composition, wherein the same quantity or less of titanylphthalocyanine as metal-free phthalocyanine is added to the metal-free phthalocyanine and, thereafter, crystal transformation is conducted by stirring. Japanese Patent Laid-Open Publication No. H4(1992) 351673 discloses a mixed crystal comprising oxytitanium phthalocyanine and at least one kind of hydroxymetal phthalocyanine. Japanese Patent Laid-Open Publication No. H4(1992) 184452 discloses an applying solution, which is used for photoreceptors, containing titanylphthalocyanine and a multilayer type phthalocyanine derivative. Japanese Patent Laid-Open Publication No. H8(1996) 67829 discloses a production method of a phthalocyanine mixed crystal, comprising: dissolving at least two kinds of phthalocyanine-based compounds in acid; and adding this solution to a mixture solution of water and an organic solvent having a dielectric constant of 20 or less so as to precipitate as the phthalocyanine mixed crystal. Japanese Patent Laid-Open Publication No. 2002-12790 discloses a mixed crystal comprising at least three kinds of phthalocyanine each having different central substance.

Further, Japanese Patent Laid-Open Publication No. H9(1997) 217020 discloses a μ-oxo aluminum phthalocyanine dimer having a new polymorph, and Japanese Patent Laid-Open Publication No. H10(1998) 88023 discloses a μ-oxo gallium phthalocyanine dimer. In addition, Japanese Patent Laid-Open Publication No. H7(1995) 295259 discloses an alkoxy bridged metal phthalocyanine dimer.

With regard to a μ-oxo heterometal phthalocyanine dimer, Japanese Patent Laid-Open Publication No. 2000-219817 discloses a μ-oxo aluminum/gallium phthalocyanine dimer. The phthalocyanine dimer described therein, however, is stochastically inevitably obtained as a mixture of three kinds which additionally contains a μ-oxo aluminum phthalocyanine dimer, a μ-oxo gallium phthalocyanine dimer.

Further, U.S. Pat. No. 4,900,817 discloses a polycyclic phthalocyanine compound such as (HO)GePc-O—SiPcOSi $(C_6H_{13})_3$. This polycyclic phthalocyanine compound, however, has tetravalent Si and Ge as central metal thereof. In addition, a production method thereof employs dehydration of hydroxy-substituted metal(IV) phthalocyanine in an organic solvent.

SUMMARY OF THE INVENTION

It is an object of the present invention to provide new μ-oxo bridged heterometal naphthalo/naphthalocyanine compound, phthalo/naphthalocyanine compound or naphthalo/phthalocyanine compound (in the specification, these compounds may be inclusively referred to as "μ-oxo bridged heterometal compound"), which can make the photo-functional materials to have diversified properties. It is another object of the present invention to provide a production method by which a μ-oxo bridged heterometal compound can be obtained simply, selectively and with high yield.

More specifically, the present invention provides a μ-oxo bridged heterometal naphthalo/naphthalocyanine compound (hereinafter, described as NcM1-O-M2Nc) represented by the following formula I:

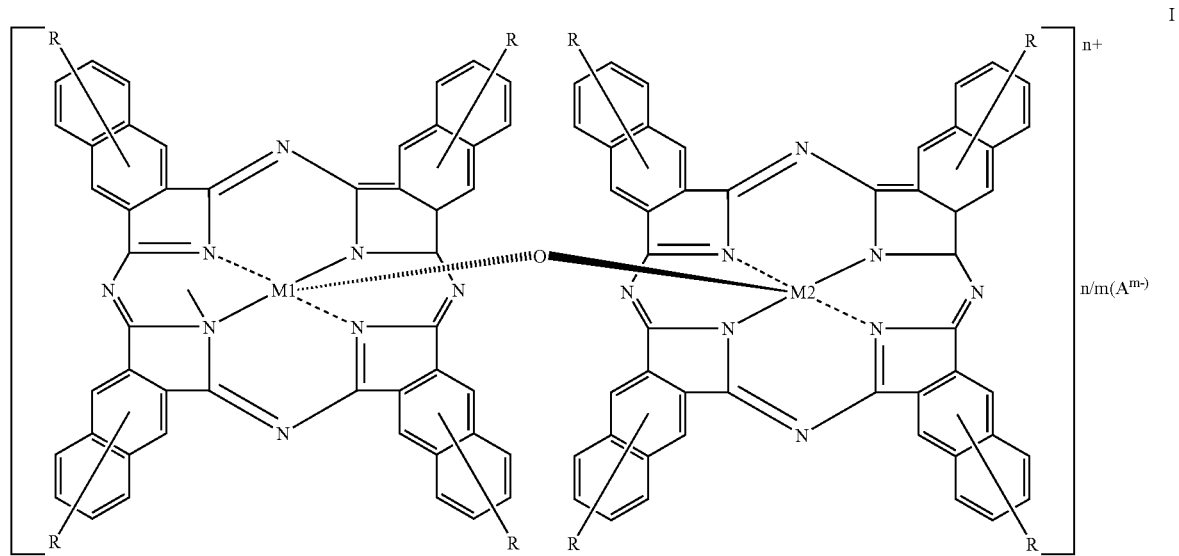

wherein M1 represents a metal atom which is able to have a valence of up to three, M2 represents a metal atom which is able to have a valence of four or five, R represents each independently one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

The present invention also provides a μ-oxo bridged heterometal phthalo/naphthalocyanine compound (hereinafter, described as PcM1-O-M2Nc) represented by the following formula II:

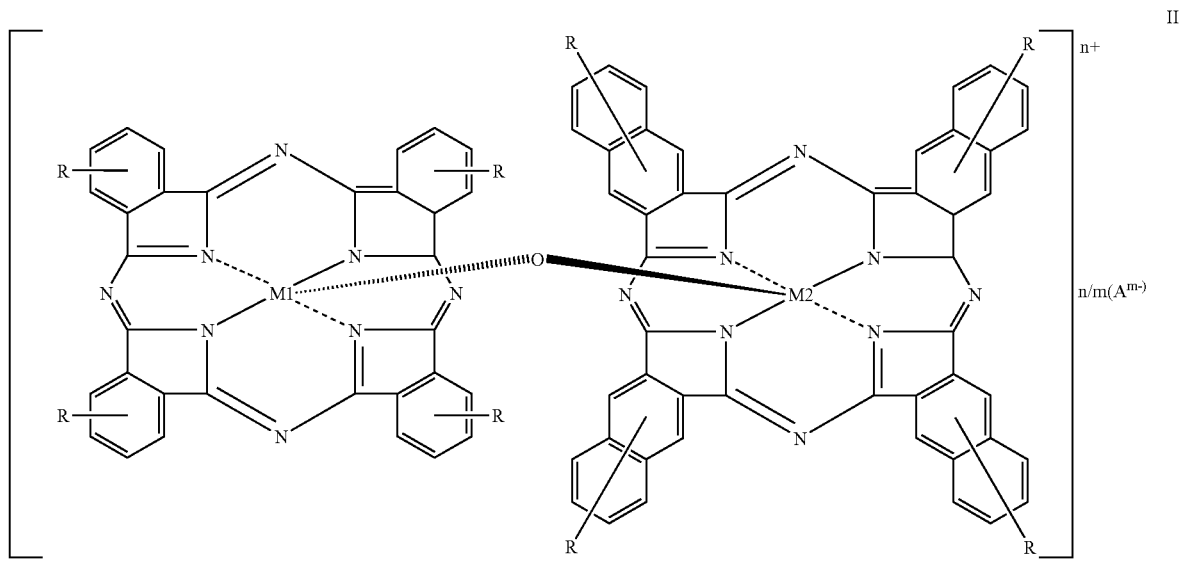

wherein M1, M2, R, n, n/m and ($A^{m-}$) have the same meanings as defined above.

The present invention also provides a µ-oxo bridged heterometal naphthalo/phthalocyanine compound (hereinafter, described as NcM1-O-M2Pc) represented by the following formula III:

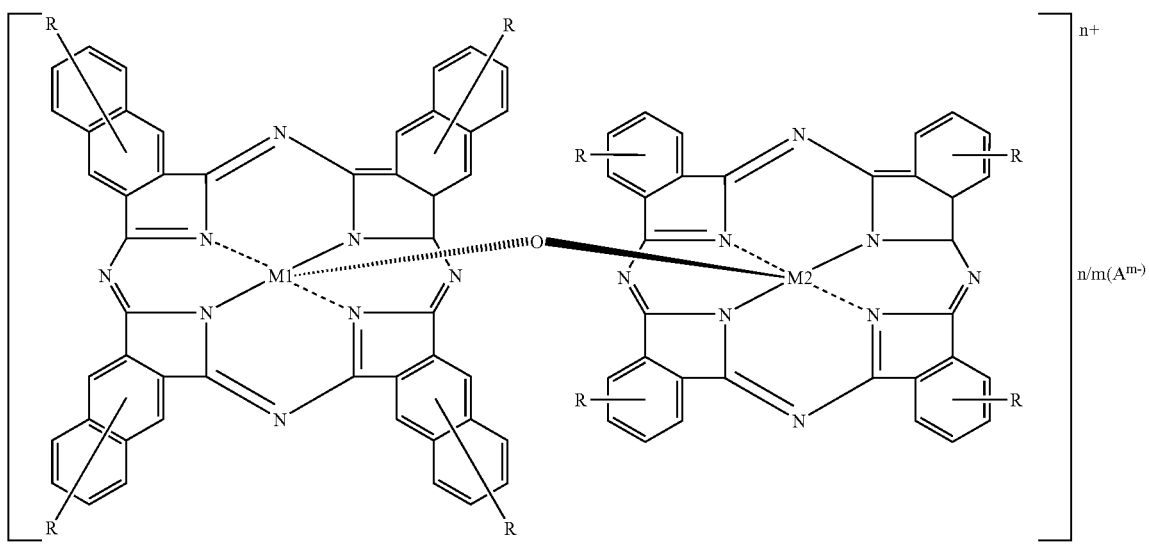

wherein M1, M2, R, n, n/m and ($A^{m-}$) have the same meanings as defined above.

The present invention also provides a production method of the µ-oxo bridged heterometal naphthalo/naphthalocyanine compound (NcM1-O-M2Nc) (the formula I), comprising the step of reacting naphthalocyanine having halometal (III) as central metal thereof with naphthalocyanine having oxymetal(IV or V) as central metal thereof by equivalent moles to each other.

The present invention also provides a production method of the compound of the formula II (PcM1-O-M2Nc) or the formula III (NcM1-O-M2Pc), comprising the step of reacting phthalocyanine or naphthalocyanine having halometal (III) as central metal thereof with naphthalocyanine or phthalocyanine having oxymetal(IV or V) as central metal thereof, respectively, by equivalent moles to each other.

The present invention further provides a production method of the compounds represented by the formulae I to III, comprising the steps of: reacting naphthalocyanine or phthalocyanine having halometal (III) as central metal thereof with naphthalocyanine or phthalocyanine having oxymetal(IV or V) as central metal thereof by equivalent moles to each other; and stabilizing the obtained compound by using aqueous ammonia.

DETAILED DESCRIPTION OF THE INVENTION

Figure 1:
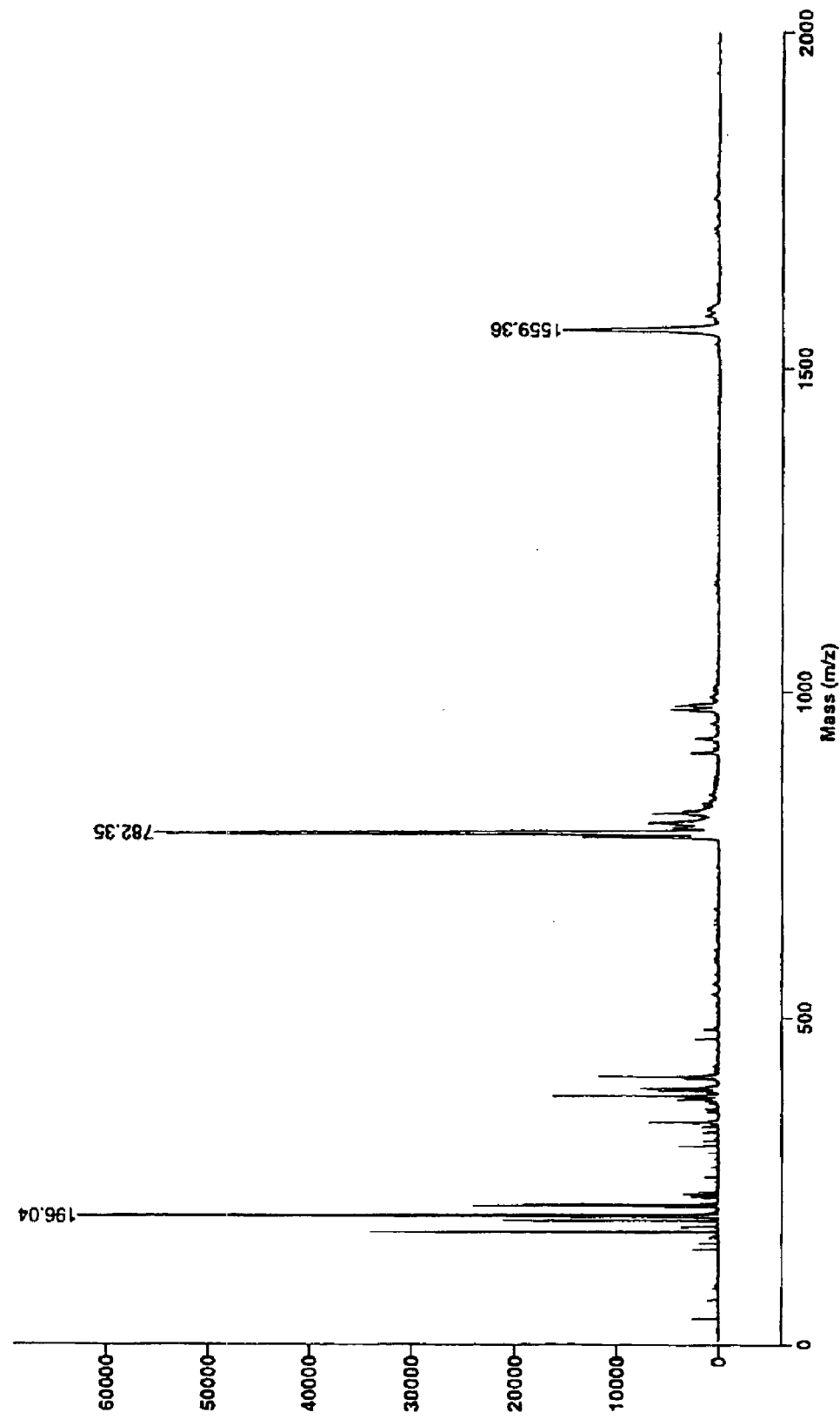
FIG. 1 is a TOF-MS spectrum of Example 1.

Among µ-oxo bridged heterometal compounds of the present invention, the NcM1-O-M2Nc compound has a structure of that central metal atoms (M1, M2) in metal naphthalocyanine including M1 as central metal thereof and metal naphthalocyanine including M2 as central metal thereof, are oxo bridged. The PcM1-O-M2Nc is a compound having a structure of that central metal atoms (M1, M2) in metal phthalocyanine including M1 as central metal thereof and metal naphthalocyanine including M2 as central metal thereof, are oxo bridged. The NcM1-O-M2Pc is a compound having a structure of that central metal atoms (M1, M2) in metal naphthalocyanine including M1 as central metal thereof and metal phthalocyanine including M2 as central metal thereof, are oxo bridged. M1 means a metal atom which is able to have a valence of up to three and, for example, involves a metal atom of the 3A group (such as Sc and Y) or the 3B group (such as Al, Ga, In and Tl) on the periodic table. M2 means a metal atom which is able to have a valence of four or five and, for example, involves a metal atom of the 4A to 7A groups, the 8 group and the 4B to 6B groups on the periodic table. A metal atom of the 3A group or the 3B group on the periodic table (such as Al and Ga) is not included in M2. Meanwhile, M2 may exist as a trivalent form when it is included in the structure of the µ-oxo bridged heterometal compound.

An NcM1-O-M2Nc compound, a PcM1-O-M2Nc compound or an NcM1-O-M2Pc compound as a µ-oxo bridged heterometal compound of the present invention may each have one or more substituent groups and/or substituent atoms (R) on the aromatic rings thereof. The kind of the substituent groups and the substituent atoms is not particularly limited as long as it exists with stability in the compounds, and specific examples thereof include an alkyl group (such as a methyl group, an ethyl group, a propyl group, an isopropyl group, a butyl group, a tert-butyl group and an isoamyl group), an alkoxy group (such as a methoxy group, an ethoxy group, an isopropoxy group and a butoxy group), a phenoxy group, an aryl group (such as a phenyl group and a tolyl group), an aralkyl group (such as a benzyl group), an allyl group, an alkenyl group, a cyano group, a halogen atom (such as Cl, Br, I and F), a carboxylate group, a sulfonate group, a nitro group, an amino group, and the like.

In addition, a µ-oxo bridged heterometal compound of the present invention may carry positive charge (n+) corresponding to a valence of central metal atom (M2) and, therefore, typically exists in a form of being accompanied by a proper counteranion (A) in a solution. Examples of the counteranion (A) include a monovalent inorganic anion such as hydroxy ion (OH⁻), halogen ion (for example, Cl⁻) and hydrogen sulfate ion ($HSO_4^-$), or a divalent inorganic anion such as sulfate ion ($SO_4^{2-}$). A preferable counteranion (A) is a hydroxy ion (OH⁻) as in the case of washing with aqueous ammonia after reacting.

The µ-oxo bridged heterometal compound is produced by reacting naphthalocyanine having halometal (III) as central metal thereof (hereinafter, referred to as halometal(III) naphthalocyanine) or phthalocyanine having halometal (III) as central metal thereof (hereinafter, referred to as halometal (III) phthalocyanine) with naphthalocyanine having oxymetal(IV or V) as central metal thereof (hereinafter, referred to as oxymetal(IV or V) naphthalocyanine) or phthalocyanine having oxymetal(IV or V) as central metal thereof (hereinafter, referred to as oxymetal(IV or V) phthalocyanine).

Halometal(III) naphthalocyanine is represented, for example, by the following formula A-1:

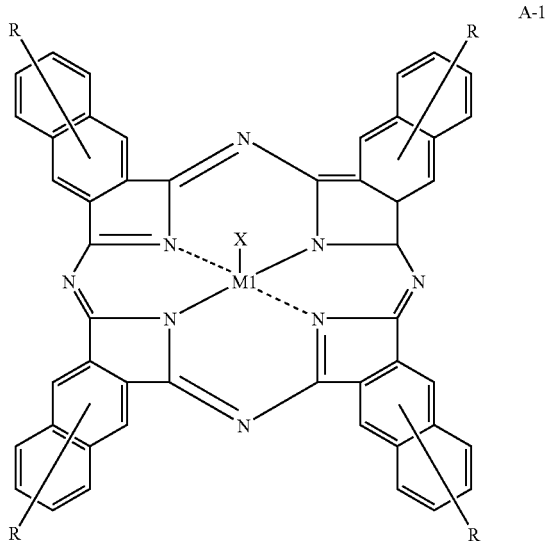

A-1 wherein R and M1 have the same meanings as defined above, and X represents a halogen atom.

Halometal(III) phthalocyanine is represented, for example, by the following formula A-2:

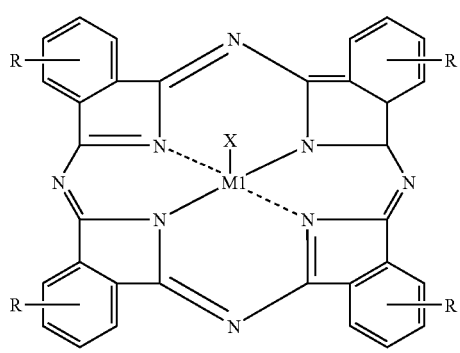

A-2 wherein R and M1 have the same meanings as defined above, and X represents a halogen atom.

Halometal(III) naphthalocyanine can be obtained by using a well-known method; for example, to react 2,3-dicyanonaphthalene or a derivative thereof together with a halide of trivalent metal atom in a high-boiling organic solvent such as 1-chloronaphthalene or quinoline. In addition, the product can be washed with hot DMF, DMF and the like after being filtered under heating. A halogen atom of the halide is fluorine, chlorine, bromine or iodine, preferably chlorine.

The halometal(III) phthalocyanine can also be synthesized in the same manner as that described above except that phthalonitrile, 1,3-diiminoisoindoline or a derivative thereof is employed instead of the 2,3-dicyanonaphthalene or the derivative thereof.

Preferable examples of central metal atom M1 of the halometal(III) naphthalocyanine or the halometal(III) phthalocyanine include aluminum Al(III) and gallium Ga(III). Indium In(III), however, is not preferred as M1. Indium is easily eliminated from the naphthalocyanine ring or the phthalocyanine ring by sulfuric acid treatment, metal-free naphthalocyanine or phthalocyanine would be produced, and reaction of the present invention would become difficult to occur.

Examples of halometal(III) naphthalocyanine preferably include chlorogallium naphthalocyanine and chloroaluminum naphthalocyanine. Examples of halometal(III) phthalocyanine preferably include chlorogallium phthalocyanine and chloroaluminum phthalocyanine.

Oxymetal(IV or V) naphthalocyanine is represented, for example, by the following formula B-1:

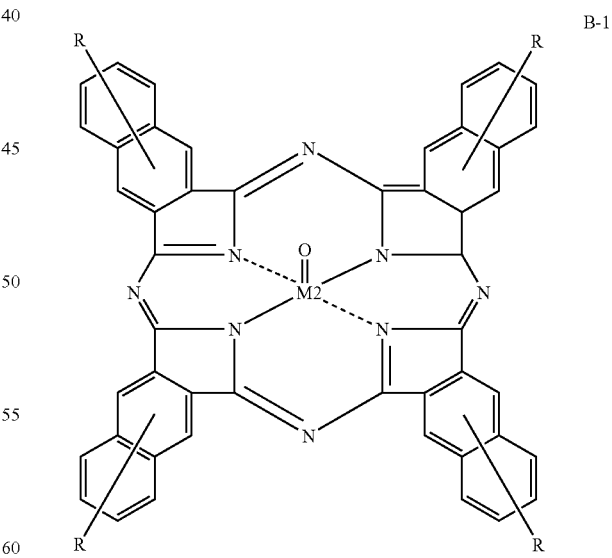

B-1 wherein R and M2 have the same meanings as defined above.

In addition, oxymetal(IV or V) phthalocyanine is represented, for example, by the following formula B-2:

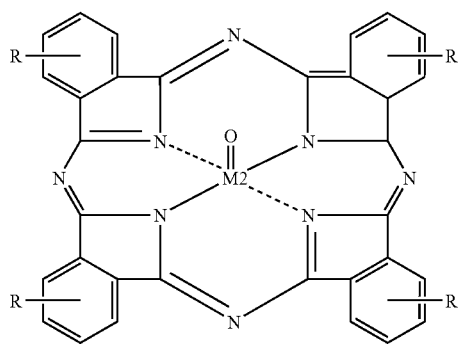

B-2 wherein R and M2 have the same meanings as defined above.

Oxymetal(IV or V) naphthalocyanine can be obtained by using a well-known method; for example, to react 2,3-dicyanonaphthalene or a derivative thereof together with a halide of metal atom having a valence of three to six (such as titanium chloride, vanadyl chloride and molybdenum chloride) in a high-boiling organic solvent such as 1-chloronaphthalene or quinoline and, then, to hydrolyze the obtained metal (di)halide phthalocyanine. The hydrolysis may be caused by washing with DMF and the like; however, it is preferably conducted in dilute hydrochloric acid as required.

The oxymetal(IV or V) phthalocyanine can also be synthesized in the same manner as that described above except that phthalonitrile, 1,3-diiminoisoindoline or a derivative thereof is employed instead of the 2,3-dicyanonaphthalene or the derivative thereof.

Examples of central metal atom M2 of the oxymetal(IV or V) naphthalocyanine or oxymetal(IV or V) phthalocyanine include titanium Ti, vanadium V, molybdenum Mo, palladium Pd and the like. Preferable oxymetal(IV or V) naphthalocyanine is titanyl naphthalocyanine O=TiNc, vanadyl naphthalocyanine O=VNc, oxymolybdenum naphthalocyanine O=MoPc. Preferable oxymetal(IV or V) phthalocyanine includes titanyl phthalocyanine O=TiPc, vanadyl phthalocyanine O=VPc, and oxymolybdenum phthalocyanine O=MoPc. In particular, titanyl naphthalocyanine and titanyl phthalocyanine are preferable.

For example, titanyl naphthalocyanine can be generally obtained by reacting 2,3-dicyanonaphthalene together with titanium chloride (such as titanium tetrachloride) in a high-boiling organic solvent such as 1-chloronaphthalene or quinoline and, then, hydrolyzing the obtained chlorotitanium naphthalocyanine. Alternatively, the titanyl naphthalocyanine can be generally obtained by heat-refluxing 2,3-dicyanonaphthalene and titanium tetrachloride in an alcohol solvent in the presence of a reaction accelerator (such as 1,8-diazabicyclo[5,4,0]unde-7-cene (DBU) or 1,5-diazabicyclo[4,3,0]-5-nonene (DBN)), and hydrolyzing the obtained dichlorotitanium naphthalocyanine in dilute hydrochloric acid. Titanyl phthalocyanine can also be synthesized in the same manner as that described above except that phthalonitrile or 1,3-diiminoisoindoline is employed instead of the 2,3-dicyanonaphthalene (Japanese Patent Laid-Open Publication No. H3(1991) 21669).

A μ-oxo bridged heterometal compound of the present invention can be produced by reacting the halometal(III) naphthalocyanine or halometal(III) phthalocyanine with oxymetal(IV or V) naphthalocyanine or oxymetal(IV or V) phthalocyanine. For example, an NcM1-O-M2Nc compound can be produced by reacting the halometal(III) naphthalocyanine with oxymetal(IV or V) naphthalocyanine. Halometal(III) naphthalocyanine or halometal(III) phthalocyanine and oxymetal(IV or V) naphthalocyanine or oxymetal(IV or V) phthalocyanine are preferably employed in a molar ratio of 1 to 1, namely, equivalent moles to each other. The reason therefor is that the reaction at this molar ratio enables an intended μ-oxo bridged heterometal compound to be selectively obtained with high yield.

An example of the reaction includes a method of reacting with mixing halometal(III) naphthalocyanine or halometal(III) phthalocyanine with oxymetal(IV or V) naphthalocyanine or oxymetal(IV or V) phthalocyanine by equivalent moles to each other in the presence of concentrated sulfuric acid. A sulfuric acid having a concentration of 95% or more is preferably used as the concentrated sulfuric acid.

Specifically, halometal(III) naphthalocyanine or halometal(III) phthalocyanine can be reacted with oxymetal(IV or V) naphthalocyanine or oxymetal(IV or V) phthalocyanine for 2 to 3 hours by dissolving in concentrated sulfuric acid under the conditions of cooling (such as a temperature of 5° C. or less). Further, a compound can be precipitated by pouring the reacted compound onto a large quantity of water/ice after this reaction. The compound is finely divided and refined by this step.

The treatment, such that reaction products and the like are dissolved in concentrated sulfuric acid, and the solution is poured onto water/ice to precipitate a solid thereof so as to be finely divided and refined, is referred to as "acid pasting treatment". In the present invention, halometal(III) naphthalocyanine or halometal(III) phthalocyanine is reacted with oxymetal(IV or V) naphthalocyanine or oxymetal(IV or V) phthalocyanine by the so-called acid pasting treatment to obtain a μ-oxo bridged heterometal compound.

After the reaction, the obtained compound is treated with aqueous ammonia to remove an acid root from the reacted compound and to stabilize the compound. Specifically, the reacted compound is added to water and ammonia solution, the filtered-out compound is sufficiently washed with water and ion exchange water, and it is dried to refine the compound easily. The aqueous ammonia to be preferably used has a concentration of 1% or more, preferably 5 to 50%, and particularly the aqueous ammonia having a concentration of 25% is preferably used.

This method enables a μ-oxo bridged heterometal compound of the present invention to be produced simply, selectively and with high yield.

Examples of the preferable combination of halometal(III) naphthalocyanine/oxymetal(IV or V) naphthalocyanine for producing an NcM1-O-M2Nc compound of the present invention represented by the formula I include chlorogallium naphthalocyanine/titanyl naphthalocyanine, chlorogallium naphthalocyanine/vanadyl naphthalocyanine, chloroaluminum naphthalocyanine/titanyl naphthalocyanine, chloroaluminum naphthalocyanine/oxymolybdenum naphthalocyanine, chlorogallium naphthalocyanine/oxymolybdenum naphthalocyanine, chlorogallium naphthalocyanine/oxypalladium naphthalocyanine, and the like. Further, these halometal(III) naphthalocyanine/oxymetal(IV or V) naphthalocyanine may have one or more substituent groups and/or substituent atoms on the aromatic rings thereof A similar combination is also preferable with regard to a PcM1-O-M2Nc compound of the present invention represented by the formula II. Examples of the combination include chlorogallium phthalocyanine/titanyl naphthalocyanine, chloroaluminum phthalocyanine/titanyl naphthalocyanine, chlorogallium phthalocyanine/vanadyl naphthalocyanine, chloroaluminum phthalocyanine/vanadyl naphthalocyanine, tetrakis(tert-butyl)chlorogallium phthalocyanine/titanyl naphthalocyanine, and the like.

A similar combination is also preferable with regard to an NcM1-O-M2Pc compound of the present invention represented by the formula III. Examples of the combination include chlorogallium naphthalocyanine/titanyl phthalocyanine, chloroaluminum naphthalocyanine/titanyl phthalocyanine, chlorogallium naphthalocyanine/vanadyl phthalocyanine, chloroaluminum naphthalocyanine/vanadyl phthalocyanine, tetrakis(tert-butyl)chlorogallium naphthalocyanine/tetrakis(tert-butyl)titanyl phthalocyanine, and the like.

A μ-oxo bridged heterometal compound thus obtained of the present invention represented by the formulae I to III is useful for electric charge generating materials such as organic photoreceptors, photoconductive materials, optical recording materials, organic solar cell materials, nonlinear optical materials and the like.

According to the present invention, it is possible to obtain easily a μ-oxo bridged heterometal compound, which is "D-σ-A type pigment" (that means a pigment such that donor pigment (D) and acceptor pigment (A) are connected through σ-bond (Solar Energy Materials & Solar Cells 65(2001), 133–139)), while a selective production of the 'D-σ-A type pigment' has conventionally been difficult, so that a single product thereof has been obtained by separating and refining from a mixture. This μ-oxo bridged heterometal compound is useful for electric charge generating materials such as organic photoreceptors, photoconductive materials, optical recording materials, organic solar cell materials, nonlinear optical materials and the like. According to the present invention, it is also possible to obtain a μ-oxo bridged heterometal compound, which is able to univocally induce the polarization of intramolecular electronic state, simply, selectively and with high yield by reacting halometal (III) naphthalocyanine or halometal(III) phthalocyanine with oxymetal(IV or V) naphthalocyanine or oxymetal(IV or V) phthalocyanine.

EXAMPLES

The following Examples further illustrate the present invention in detail but are not to be construed to limit the scope thereof Synthesis Example 1
Synthesis of Titanyl Naphthalocyanine O=TiNc 4.94 g (approximately 0.0277 mol) of 2,3-dicyanonaphthalene and 20 ml of quinoline were charged and dispersed into a 100-ml three-necked flask, and 1.58 g (approximately 0.00831 mol) of titanium tetrachloride was added thereto, and it was washed, thereafter refluxed and dispersed at a temperature of 230° C. for 10 hours. After being filtered under heating (130° C.), 150 ml of hot DMF was sprinkled thereon so as to wash. 8.2 g of the wet cake obtained and 25 ml of DMF were charged into a 100-ml three-necked flask to be refluxed and dispersed for 3 hours, and filtered under heating (110° C.), thereafter, sprinkled and washed with 150 ml of hot DMF. After repeating this step three times, the obtained wet cake was sprinkled and washed with 100 ml of alcohol and 180 ml of water. 8.29 g of the wet cake subsequently obtained and 125 ml of 5%-hydrochloric acid were charged into a 200-ml beaker to be dispersed at room temperature for 6 hours. After being filtered at a reduced pressure, 200 ml of water and 3000 ml of ion exchange water (pH: 4.80, conductivity: 8.97 μs/cm in final filtrate) was sprinkled on the obtained wat cake so as to wash, and thereafter dried at a temperature of 80° C. to obtain 3.53 g of titanyl naphthalocyanine O=TiNc (yield: 65.6%).

Synthesis Example 2
Synthesis of Titanyl Phthalocyanine O=TiPc (A Method Described in Example 1 of Japanese Patent Laid-Open Publication No. H3(1991) 21669)

91.8 g (approximately 0.6 mol) of 1,8-diazabicyclo[5,4,0]unde-7-cene (DBU) was dropped into a mixture of 76.2 g (approximately 0.6 mol) of phthalonitrile, 56.4 g (approximately 0.3 mol) of titanium tetrachloride and 200 ml of n-amyl alcohol under heat-reflux for approximately 1 hour, and further stirred under heat-reflux for 6 hours. After the reaction was completed, the mixture stood to cool to a temperature of 100° C., approximately 30 ml of water was added thereto, and it was stirred for a while, and thereafter the product was filtered, sprinkled and washed with 100 ml of dimethylformamide (DMF) and subsequently 100 ml of methanol. The obtained dichlorotitanium phthalocyanine was dispersed into 1000 ml of 3%-hydrochloric acid and washed with water so that pH becomes 6 or more. Next, this water-wet cake was put into approximately 500 ml of DMF previously heated to a temperature of 100 to 120° C., stirred at this temperature for approximately 1 hour, and thereafter filtered under heating. The obtained DMF-wet cake was washed with 100 ml of methanol, dried to obtain 29.1 g of titanyl phthalocyanine O=TiPc.

Synthesis Example 3
Synthesis of Vanadyl Naphthalocyanine O=VNc

The same manner as Synthesis Example 1 was conducted except that 0.54 g (0.00344 mol) of vanadium trichloride was employed instead of the titanium tetrachloride employed in Synthesis Example 1, and 2.23 g (0.0125 mol) of the 2,3-dicyanonaphthalene was employed to obtain 1.38 g of vanadyl naphthalocyanine O=VNc (yield: 56.6%).

Synthesis Example 4
Synthesis of Vanadyl Phthalocyanine O=VPc

The same procedure as Synthesis Example 2 was conducted except that vanadium trichloride (0.3 mol) was employed instead of the titanium tetrachloride employed in Synthesis Example 2 to obtain vanadyl phthalocyanine O=VPc.

Synthesis Example 5
Synthesis of Chlorogallium Phthalocyanine ClGaPc (A Method Described in Synthesis Example 1 of Japanese Patent Laid-Open Publication No. H10(1998) 88023)

145.5 g (1.13 mol) of phthalonitrile, 680 ml of 1-chloronaphthalene and 50.0 g (0.284 mol) of gallium (III) chloride were charged into a four-necked flask to be heated and stirred under reflux at a temperature of 255° C. for 12 hours. Thereafter, the reflux was stopped and the mixture stood to cool to a temperature of approximately 130° C., and thereafter was filtered under heating, and sprinkled and washed with 2000 ml of hot dimethylformamide (100° C.-DMF) and 1000 ml of DMF. The obtained cake was dispersed again into 1500 ml of DMF, stirred and refluxed for 3 hours, and thereafter was filtered under heating at a temperature of 110° C. to be thereafter sprinkled and washed with 1000 ml of hot DMF (110° C.) and 1000 ml of DMF. After repeating this step twice, the obtained cake was washed with 1000 ml of methanol and 1000 ml of water, thereafter dried at a temperature of 70° C. to obtain 128.8 g of chlorogallium phthalocyanine ClGaPc (yield: 73.5%).

Synthesis Example 6
Synthesis of Chlorogallium Naphthalocyanine ClGaNc

The same procedure as Synthesis Example 5 was conducted except that 2,3-dicyanonaphthalene was employed instead of the phthalonitrile in Synthesis Example 5 to obtain chlorogallium naphthalocyanine.

Synthesis Example 7
Synthesis of Chloroaluminum Phthalocyanine ClAlPc (A Method Described in Synthesis Example 1 of Japanese Patent Laid-Open Publication No. H9(1997) 217020)

180.0 g (1.41 mol) of phthalonitrile, 900 ml of 1-chloronaphthalene and 47.0 g (0.353 mol) of aluminum (III) chloride were charged into a four-necked flask, and heated and stirred under reflux at a temperature of 240° C. for 6 hours. Thereafter, the reflux was stopped and the mixture stood to cool to a temperature of approximately 130° C., and thereafter was filtered under heating, sprinkled and washed with 1800 ml of hot toluene (100° C.), 80 ml of toluene and 900 ml of acetone, and substituted with 100 ml of toluene. The obtained cake was stirred and refluxed in 750 ml of toluene for 3 hours, thereafter filtered under heating at a temperature of 100° C., and thereafter was washed with 1800 ml of hot toluene (100° C.), 180 ml of toluene and 900 ml of acetone, and the solvent was substituted with 400 ml of water. The obtained cake was added to 4500 ml of water and heat-dispersed at a temperature of 70° C. for 1 hour. After being filtered under heating, the obtained cake was washed with 900 ml of acetone and 1000 ml of water, and dried at a temperature of 70° C. to obtain 187.6 g of chloroaluminum phthalocyanine ClAlPc (yield: 92.5%).

Synthesis Example 8
Synthesis of Chloroaluminum Naphthalocyanine ClAlNc

The same procedure as Synthesis Example 7 was conducted except that 2,3-dicyanonaphthalene was employed instead of the phthalonitrile in Synthesis Example 7 to obtain chloroaluminum naphthalocyanine.

Synthesis Example 9
Synthesis of Tetrakis(tert-butyl)-chlorogallium Phthalocyanine ClGaPc(t-Bu)$_4$ The same procedure as Synthesis Example 5 was conducted except that tert-butyl-phthalonitrile was employed instead of the starting material (phthalonitrile) in Synthesis Example 5 to synthesize tetrakis(tert-butyl)-chlorogallium phthalocyanine ClGaPc(t-Bu)$_4$.

Synthesis Example 10

Chlorogallium phthalocyanine obtained in Synthesis Example 5 was dissolved in concentrated sulfuric acid and the acid pasting treatment was conducted. It is known that the product thus obtained is a mixture of hydroxygallium phthalocyanine (HOGaPc) and μ-oxo gallium phthalocyanine dimer (PcGa—O—GaPc), as described in the Journal of Chemical Society of Japan, 12, 878, 1997.

Example 1
Synthesis of μ-oxo Bridged Herometal Naphthalo/Naphthalocyanine Compound {NcGa—O—Ti$^+$Nc}OH$^-$ 44 g of concentrated sulfuric acid was cooled to a temperature of 5° C. or less and a mixture of 0.30 g (0.367 mmol) of chlorogallium naphthalocyanine ClGaNc and 0.29 g (0.367 mmol) of titanyl naphthalocyanine O=TiNc was added thereto with keeping the temperature thereof, and was stirred at a temperature of 5° C. for 2 hours. This mixture was dropped into 100 ml of water and 300 ml of ice, at a temperature of 10° C. or less to be dispersed for 2 hours. After standing, the mixture was filtered at a reduced pressure, and the obtained wet cake was sprinkled and washed with 480 ml of water. The wet cake and 200 ml of water were charged into a 500-ml beaker to be dispersed at room temperature for 2 hours. After being filtered at a reduced pressure, 200 ml of water was sprinkled on the obtained wet cake so as to wash. The wet cake, 110 ml of water and 66 ml of 25%-aqueous ammonia were charged into a 300-ml four-necked flask to be dispersed at room temperature for 6 hours. After being filtered at a reduced pressure, 350 ml of hot water and 500 ml of ion exchange water were sprinkled on the obtained wet cake so as to wash. The wet cake (1.43 g) was dried at a temperature of 70° C. to obtain 0.22 g of dark green solid represented by the following formula (yield: 38.6%).

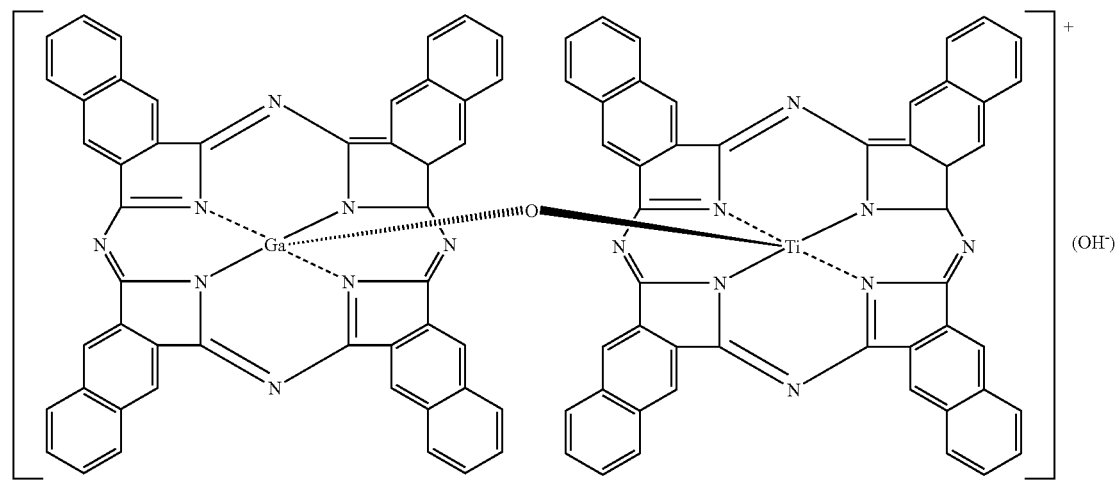

The results of elementary analysis of this compound C$_{96}$H$_{49}$N$_{16}$O$_2$GaTi (molecular weight: 1576.11) are shown in Table 1.

TABLE 1

|  | C | H | N | Ga | Ti |
|---|---|---|---|---|---|
| Calculated Value | 73.16 | 3.13 | 14.22 | 4.42 | 3.04 |
| Found Value | 72.38 | 3.16 | 13.85 | 4.52 | 2.99 |

A mass spectrum of this compound by TOF-MS (time-of-fight mass spectrum) is shown in FIG. 1.

The mass spectrum by TOF-MS was conducted by using Voyager DE (manufactured by Applied Biosystems Ltd.).

The measurement was conducted by suspending approximately 0.5 ml of the sample in 10 μl of a matrix solution of 10 mg/ml-CHCA (α-cyano-4-hydroxycinnamic acid) acetonitrile, and putting 1.0 μl thereof on a sample plate.

Example 2

Synthesis of μ-oxo Bridged Heterometal Naphthalo/Phthalocyanine Compound {NcGa—O—Ti⁺Pc}OH⁻

0.32 g of blue solid represented by the following formula (yield: 64%):

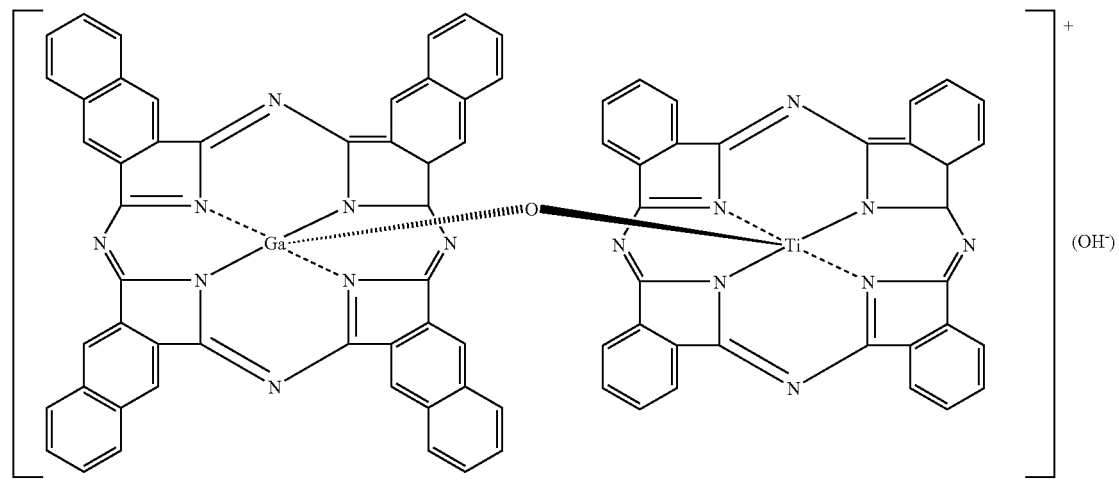

was obtained according to substantially the same manner as described in Example 1 except that a mixture of 0.30 g (0.367 mmol) of chlorogallium naphthalocyanine ClGaNc and 0.21 g (0.367 mmol) of titanyl phthalocyanine O═TiPc was employed instead of the mixture of ClGaNc and O═TiNc.

The results of elementary analysis of this compound $C_{80}H_{41}N_{16}O_2GaTi$ (molecular weight: 1375.88) are shown in Table 2.

TABLE 2

|  | C | H | N | Ga | Ti |
|---|---|---|---|---|---|
| Calculated Value | 69.84 | 3.00 | 16.29 | 5.07 | 3.48 |
| Found Value | 69.64 | 2.93 | 16.04 | 4.57 | 3.59 |

Figure 2:
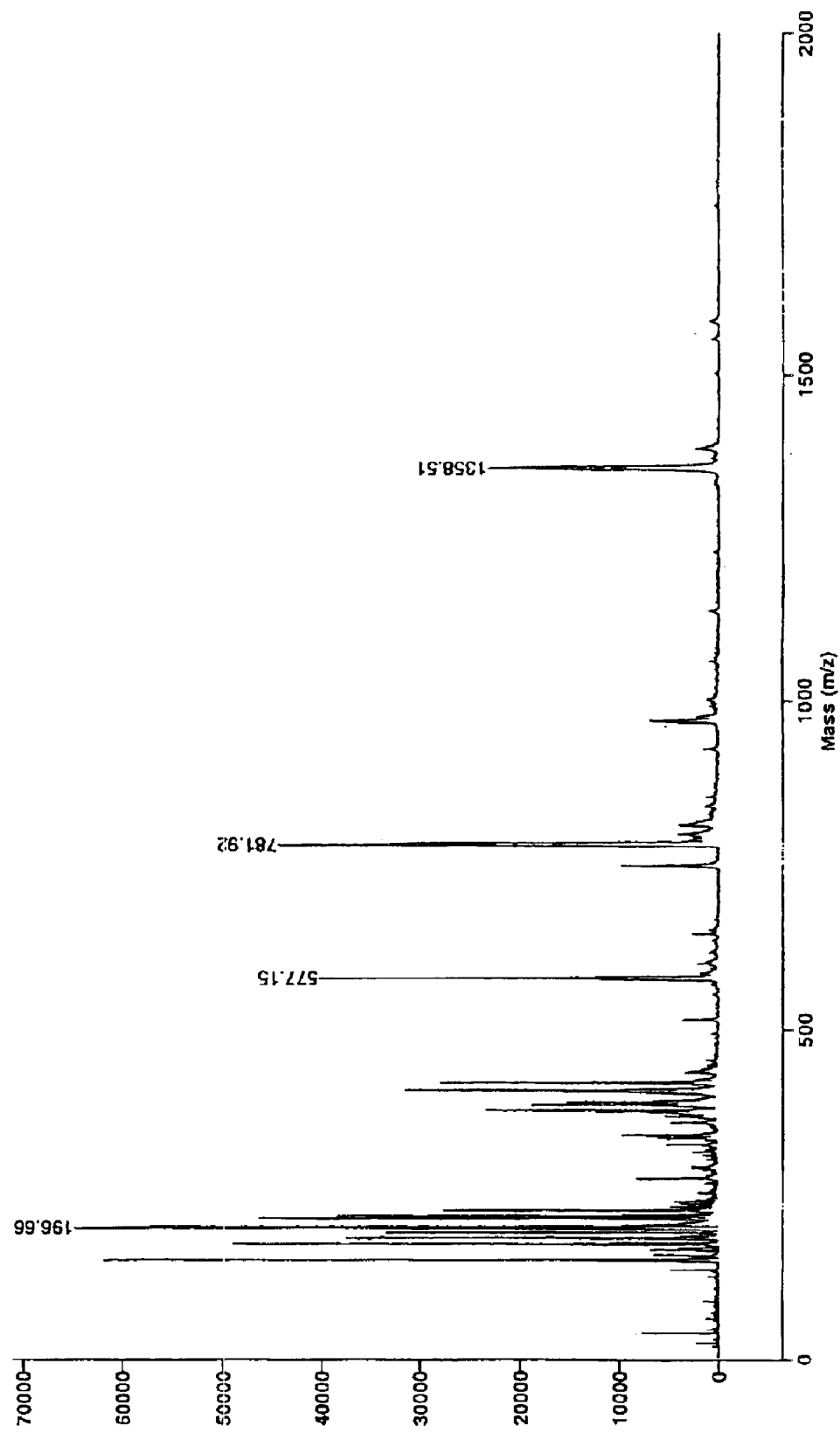
FIG. 2 is a TOF-MS spectrum of Example 2.
Figure 6:
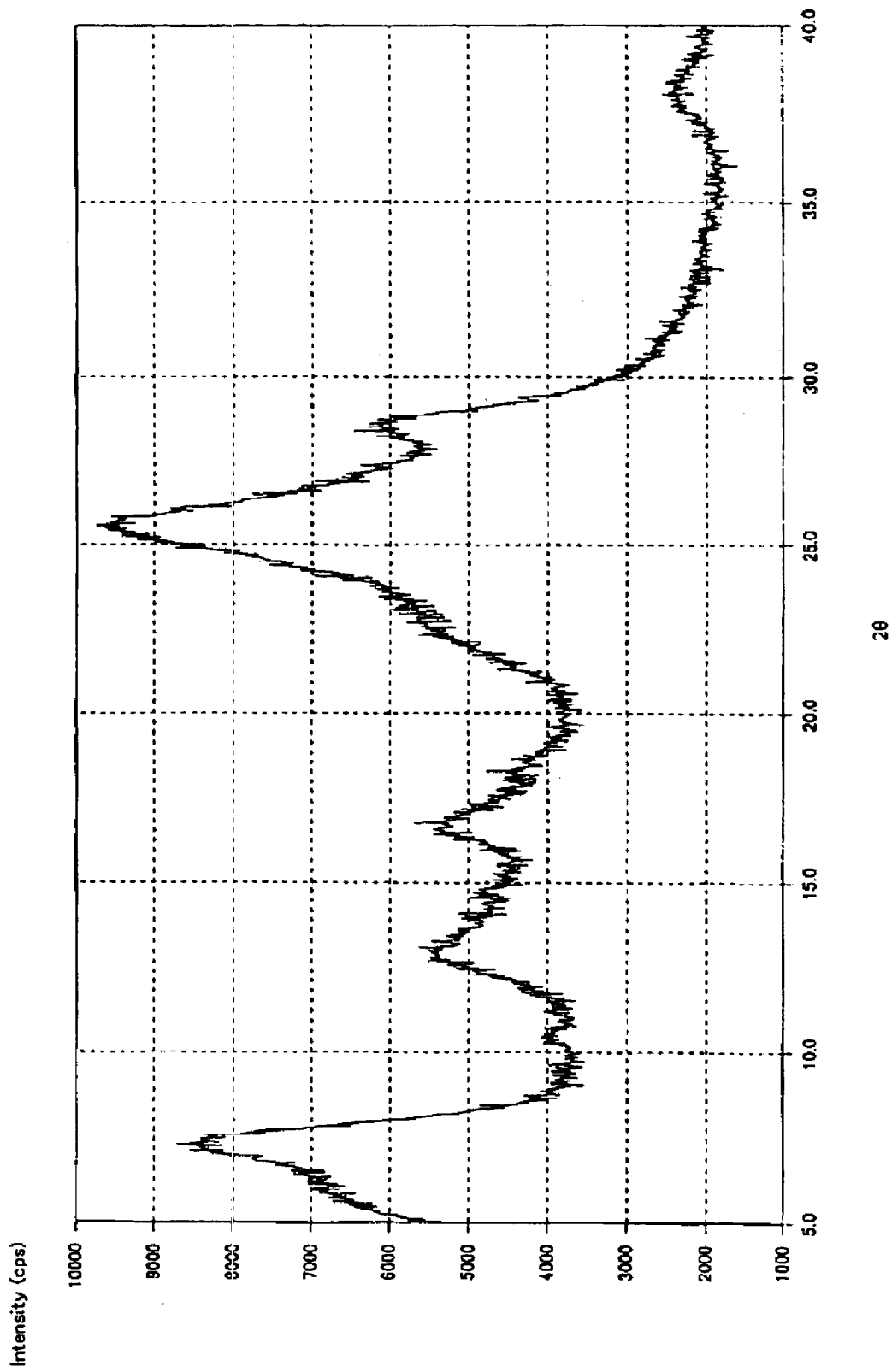
FIG. 6 is an XRD spectrum of Example 2.
Figure 7:
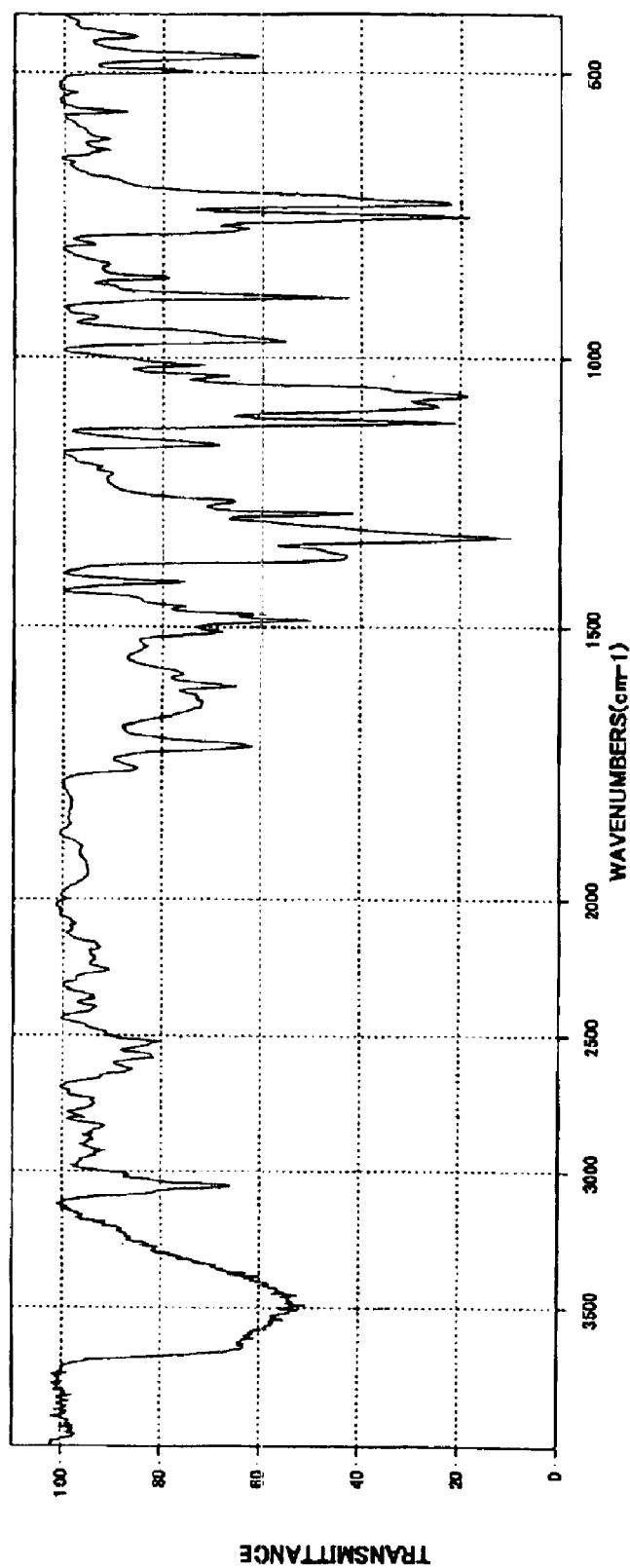
FIG. 7 is an IR spectrum of Example 2.

A mass spectrum of this compound by TOF-MS is shown in FIG. 2. In addition, an XRD spectrum of this compound is shown in FIG. 6, and an IR spectrum in FIG. 7.

Example 3

Synthesis of μ-oxo Bridged Heterometal Phthalo/Naphthalocyanine Compound {PcGa—O—Ti⁺Nc}OH⁻

0.47 g of blue-green solid represented by the following formula (yield: 71.2%):

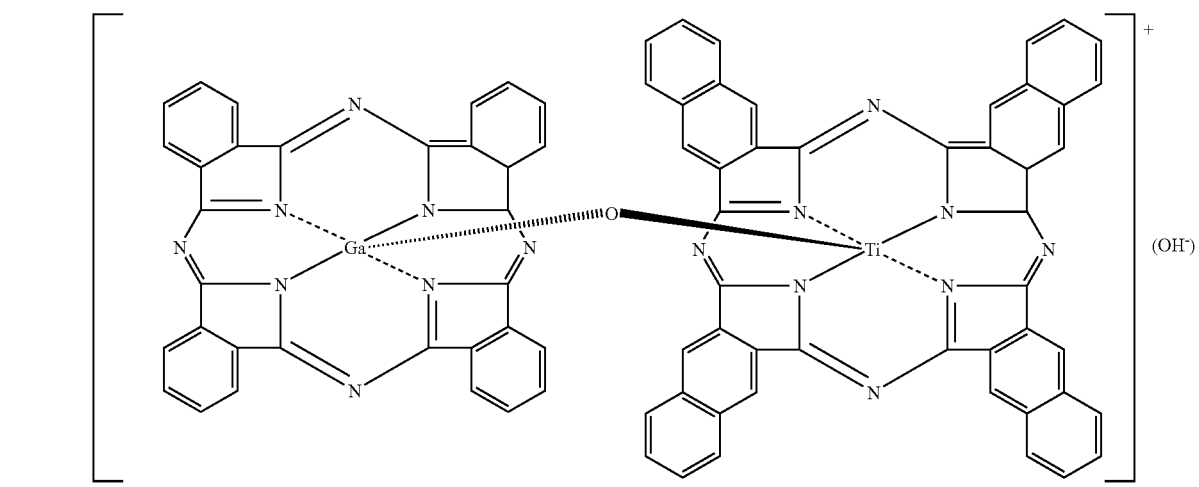

was obtained according to substantially the same manner as described in Example 1 except that a mixture of 0.30 g (0.486 mmol) of chlorogallium phthalocyanine ClGaPc and 0.38 g (0.486 mmol) of titanyl naphthalocyanine O═TiNc was employed instead of the mixture of ClGaNc and O═TiNc.

The results of elementary analysis of this compound $C_{80}H_{41}N_{16}O_2GaTi$ (molecular weight: 1375.88) are shown in Table 3.

TABLE 3

|  | C | H | N | Ga | Ti |
|---|---|---|---|---|---|
| Calculated Value | 69.84 | 3.00 | 16.29 | 5.07 | 3.48 |
| Found Value | 69.08 | 3.01 | 16.01 | 5.00 | 3.12 |

Figure 3:
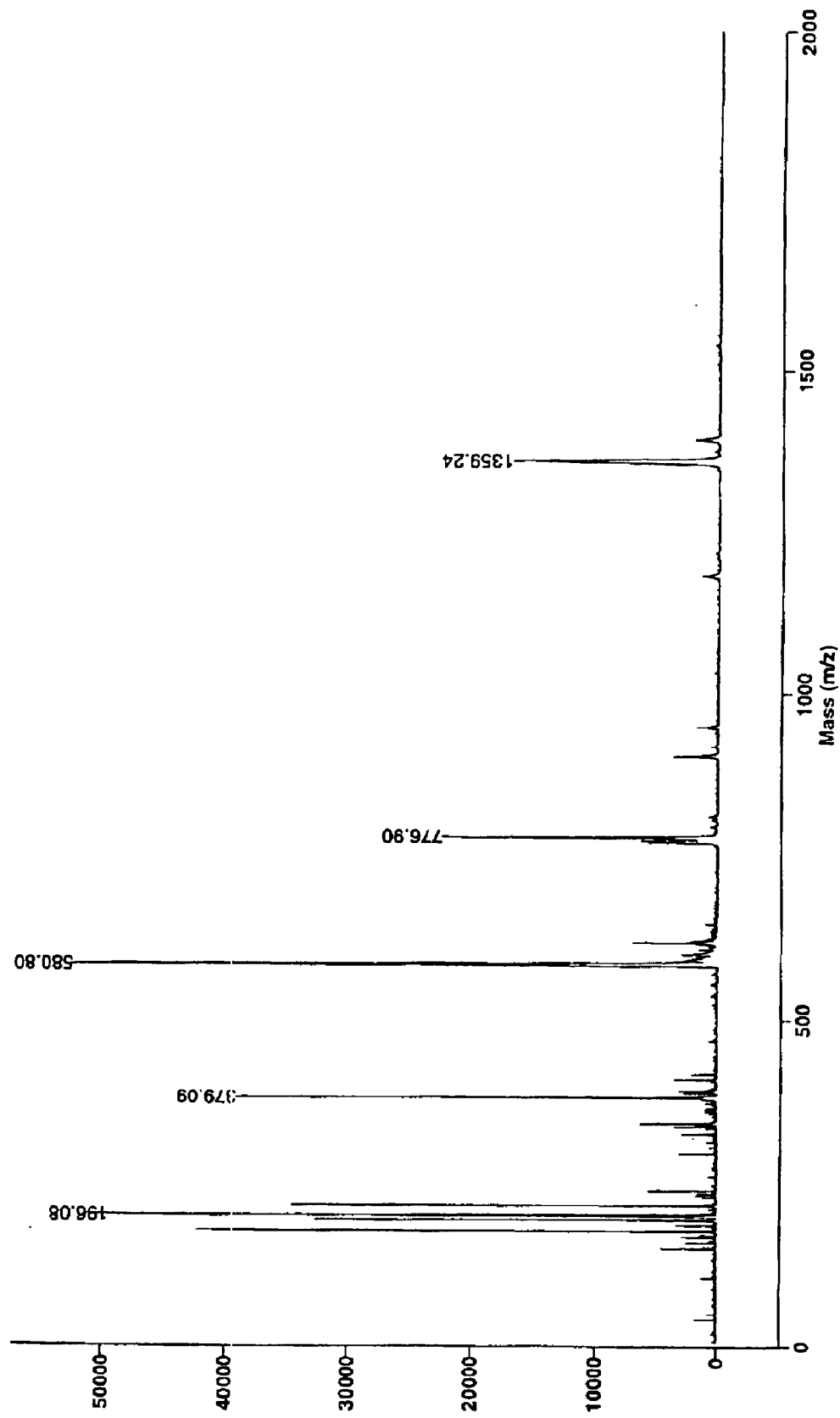
FIG. 3 is a TOF-MS spectrum of Example 3.

A mass spectrum of this compound by TOF-MS is shown in FIG. 3.

Example 4
Synthesis of μ-oxo Bridged Heterometal Naphthalo/Naphthalocyanine Compound {NcGa—O—V⁺Nc}OH⁻

0.28 g of blue-green solid represented by the following formula (yield: 49.1%):

The results of elementary analysis of this compound $C_{96}H_{49}N_{16}O_2GaV$ (molecular weight: 1579.17) are shown in Table 4.

TABLE 4

|  | C | H | N | Ga | V |
|---|---|---|---|---|---|
| Calculated Value | 73.01 | 3.13 | 14.19 | 4.42 | 3.23 |
| Found Value | 72.44 | 3.19 | 14.10 | 4.01 | 2.98 |

Example 5
Synthesis of μ-oxo Bridged Heterometal Phthalo/Naphthalocyanine Compound {PcGa—O—V⁺Nc}OH⁻

0.55 g of blue-green solid represented by the following formula (yield: 83.3%):

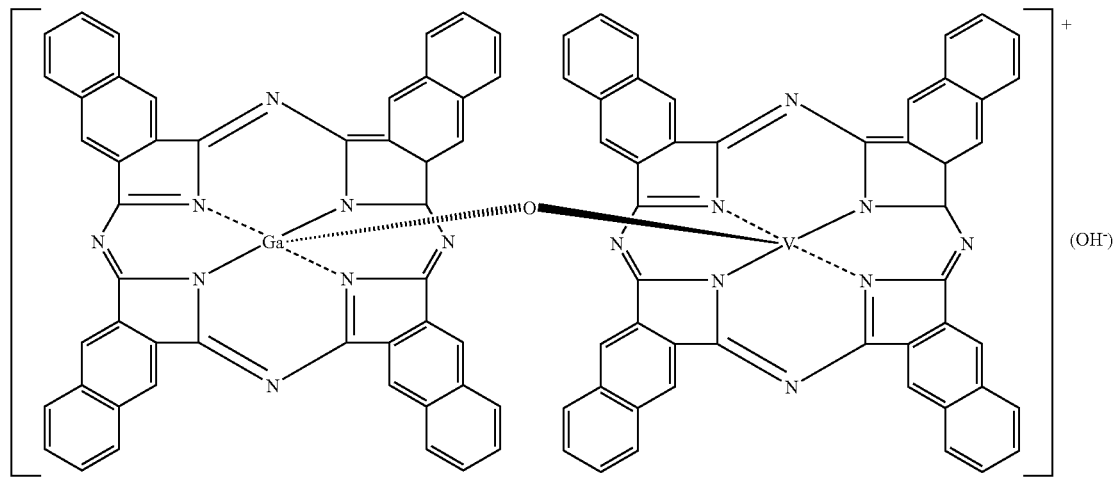

(OH⁻)

was obtained according to substantially the same manner as described in Example 1 except that a mixture of 0.30 g (0.367 mmol) of chlorogallium naphthalocyanine ClGaNc and 0.29 g (0.367 mmol) of vanadyl naphthalocyanine O=VNc was employed instead of the mixture of ClGaNc and O=TiNc.

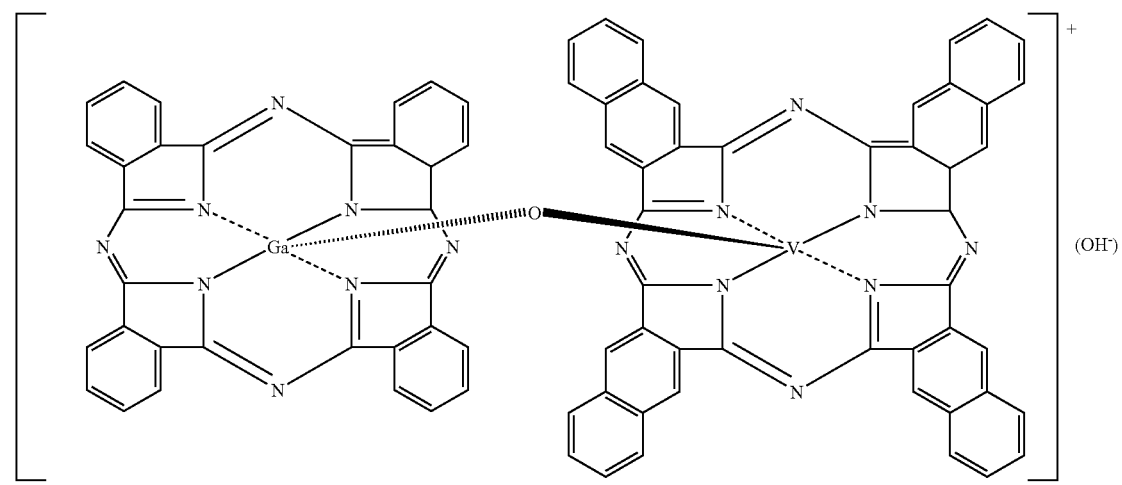

(OH⁻)

was obtained according to substantially the same manner as described in Example 1 except that a mixture of 0.30 g (0.486 mmol) of chlorogallium phthalocyanine ClGaPc and 0.38 g (0.486 mmol) of vanadyl naphthalocyanine O=VNc was employed instead of the mixture of ClGaNc and O=TiNc.

The results of elementary analysis of this compound $C_{80}H_{41}N_{16}O_2GaV$ (molecular weight: 1378.95) are shown in Table 5.

TABLE 5

|  | C | H | N | Ga | V |
|---|---|---|---|---|---|
| Calculated Value | 69.68 | 3.00 | 16.25 | 5.06 | 3.69 |
| Found Value | 68.33 | 2.99 | 15.89 | 5.38 | 3.56 |

Example 6

Synthesis of μ-oxo Bridged Herometal Naphthalo/Phthalocyanine Compound {NcGa—O—V$^+$Pc}OH$^-$ 0.34 g of dark green solid represented by the following formula (yield: 68.0%):

and 0.21 g (0.367 mmol) of vanadyl phthalocyanine O=VPc was employed instead of the mixture of ClGaNc and O=TiNc.

The results of elementary analysis of this compound $C_{80}H_{41}N_{16}O_2GaV$ (molecular weight: 1378.95) are shown in Table 6.

TABLE 6

|  | C | H | N | Ga | V |
|---|---|---|---|---|---|
| Calculated Value | 69.68 | 3.00 | 16.25 | 5.06 | 3.69 |
| Found Value | 69.16 | 2.99 | 15.82 | 4.62 | 3.37 |

Example 7

Synthesis of μ-oxo Bridged Herometal Phthalo/Naphthalocyanine Compound {PcAl—O—Ti$^+$Nc}OH$^-$ 0.53 g of dark green solid represented by the following formula (yield: 76.8%):

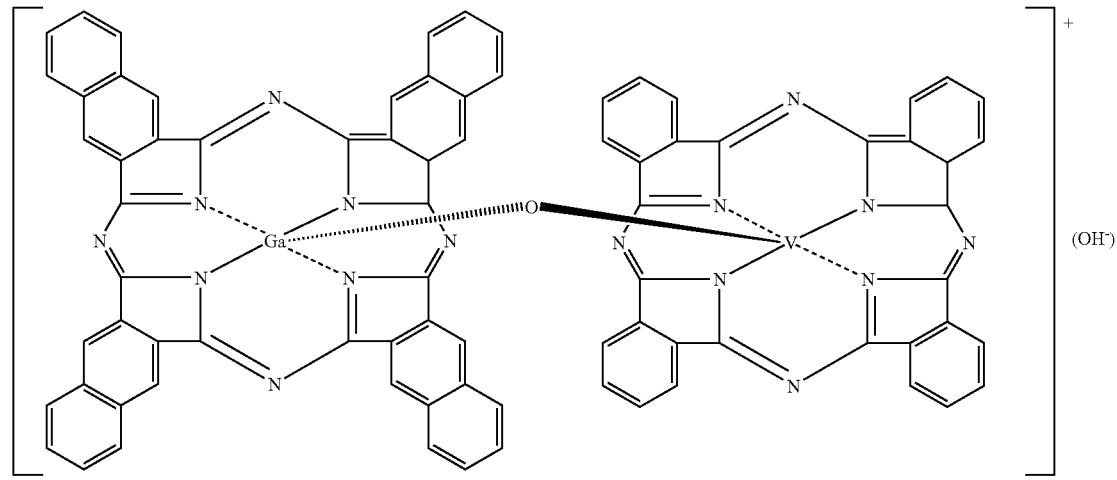

was obtained according to substantially the same manner as that described in Example 1 except that a mixture of 0.30 g (0.367 mmol) of chlorogallium naphthalocyanine ClGaNc

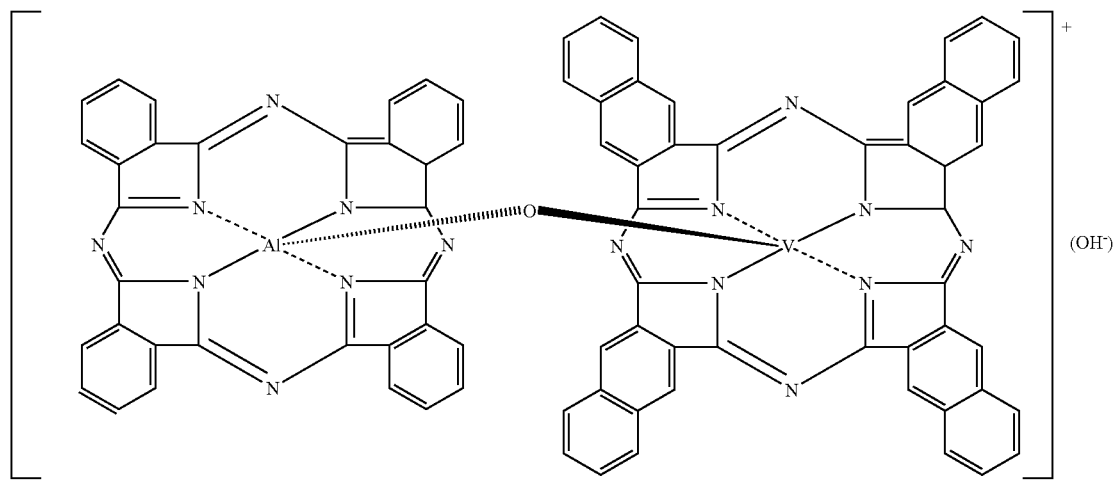

was obtained according to substantially the same manner as that described in Example 1 except that a mixture of 0.30 g (0.522 mmol) of chloroaluminum phthalocyanine ClAlPc and 0.53 g 0.522 mmol of titanyl naphthalocyanine O=TiNc was employed instead of the mixture of ClGaNc and O=TiNc.

The results of elementary analysis of this compound $C_{80}H_{41}N_{16}O_2AlTi$ (molecular weight: 1333.14) are shown in Table 7.

TABLE 7

| | C | H | N | Al | Ti |
|---|---|---|---|---|---|
| Calculated Value | 72.07 | 3.10 | 16.81 | 2.02 | 3.59 |
| Found Value | 72.01 | 3.33 | 16.02 | 1.87 | 3.82 |

Example 8

Synthesis of μ-oxo Bridged Heterometal Phthalo/Naphthalocyanine Compound {(t-Bu)$_4$PcGa—O—Ti$^+$Nc}OH$^-$ 0.41 g of blue-green solid represented by the following formula (yield: 73.2%):

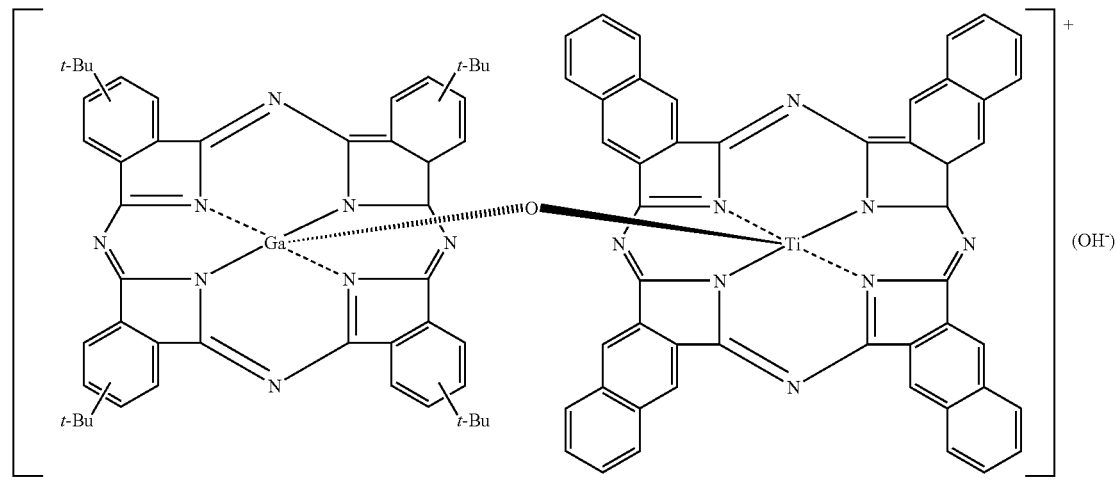

was obtained according to substantially the same manner as that described in Example 1 except that a mixture of 0.30 g (0.356 mmol) of tetrakis(tert-butyl)chlorogallium phthalocyanine ClGaPc(t-Bu)$_4$ and 0.28 g (0.356 mmol) of titanyl naphthalocyanine O=TiNc was employed instead of the mixture of ClGaNc and O=TiNc.

The results of elementary analysis of this compound $C_{96}H_{73}N_{16}O_2GaTi$ (molecular weight: 1600.30) are shown in Table 8.

TABLE 8

| | C | H | N | Ga | Ti |
|---|---|---|---|---|---|
| Calculated Value | 72.0 | 4.60 | 14.00 | 4.36 | 2.99 |
| Found Value | 71.62 | 4.64 | 13.95 | 3.99 | 2.31 |

Figure 5:
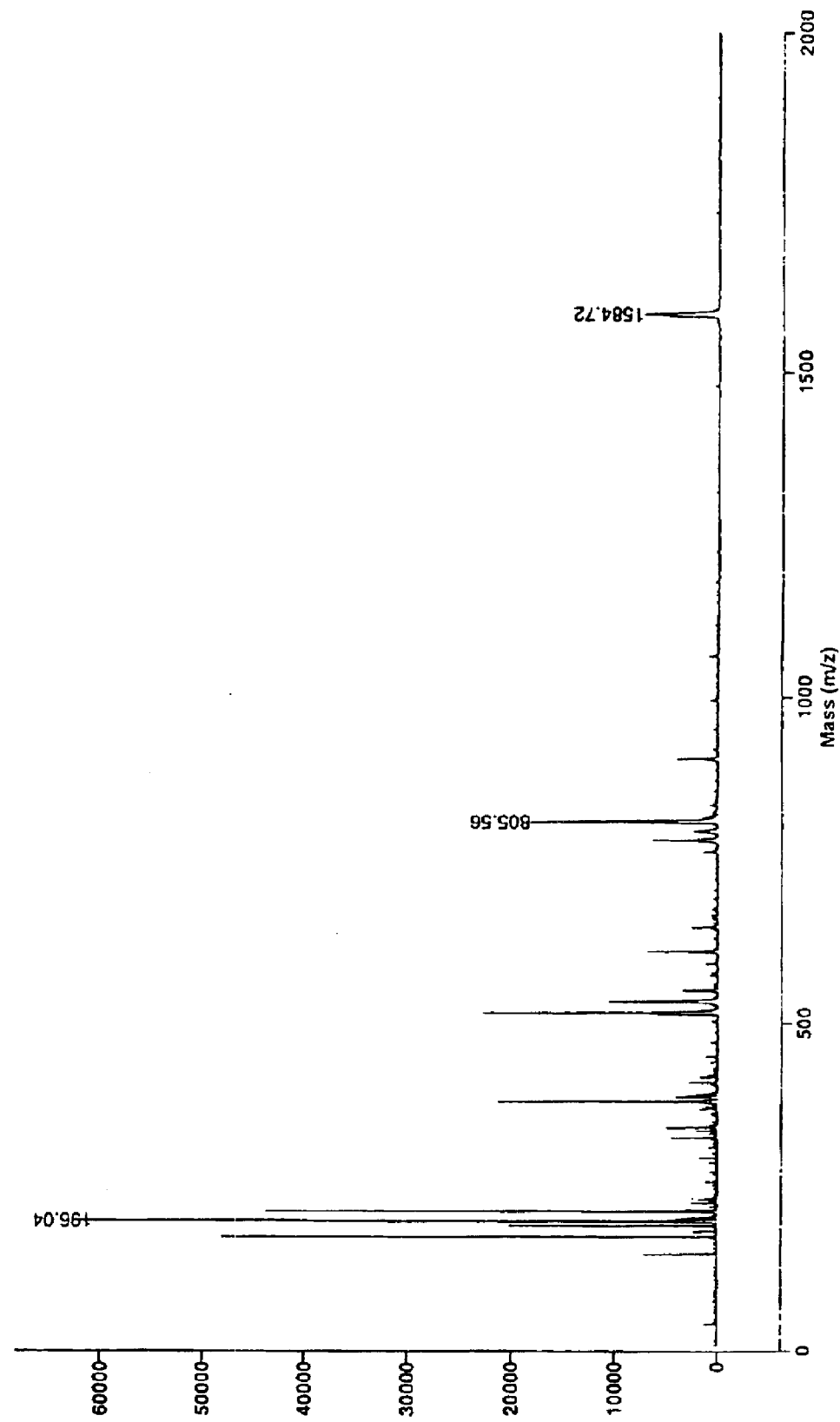
FIG. 5 is a TOF-MS spectrum of Example 8.
Figure 8:
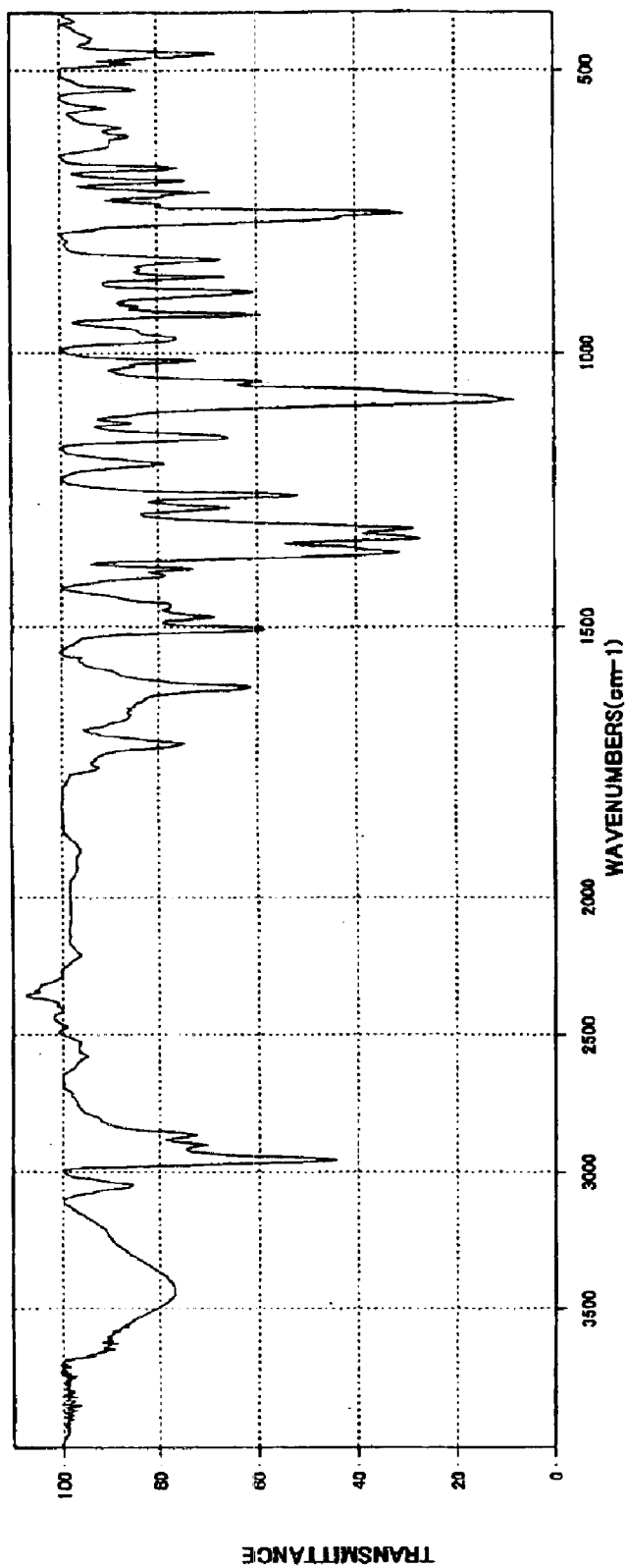
FIG. 8 is an IR spectrum of Example 8.
Figure 9:
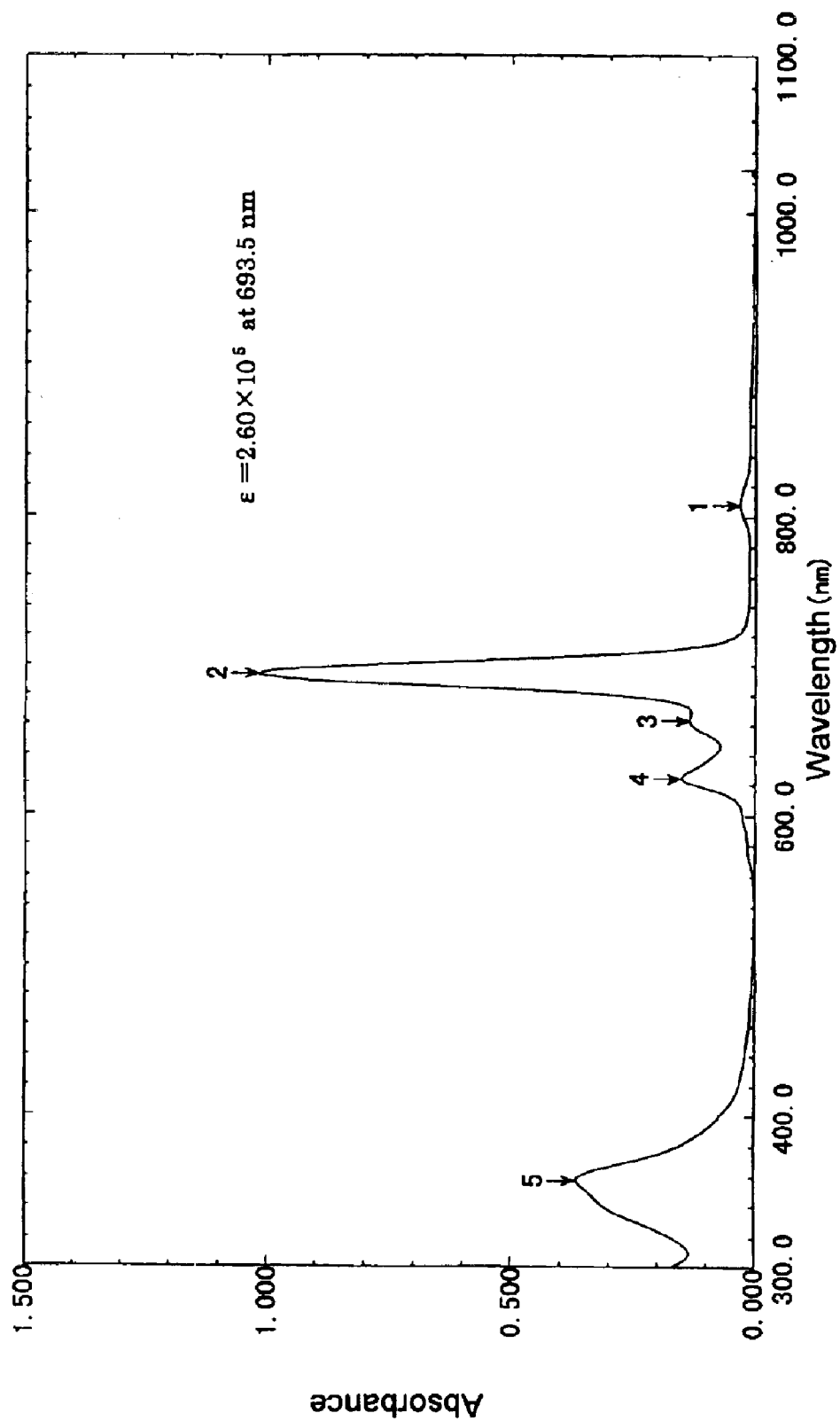
FIG. 9 is a near-ultraviolet visible near-infrared absorption spectrum of Example 8.

A mass spectrum of this compound by TOF-MS (time-of-flight mass spectrum) is shown in FIG. 5. In addition, an IR spectrum of this compound is shown in FIG. 8, and a near-ultraviolet visible near-infrared absorption spectrum in FIG. 9.

Comparative Example 1

Synthesis of μ-oxo Aluminum/Gallium Naphthalocyanine Dimer [NcAl—O—GaNc]

Referring to Example 1 of Japanese Patent Laid-Open Publication No. 2000-219817, the synthesis was conducted by mixing chloroaluminum naphthalocyanine and chlorogallium naphthalocyanine in concentrated sulfuric acid at a molar ratio of 1 to 1.

357 g of concentrated sulfuric acid was cooled by ice-methanol to a temperature of 5° C. or less and a mixture of 8.18 g (0.01 mol) of chlorogallium naphthalocyanine and 7.75 g (0.01 mol) of chloroaluminum naphthalocyanine was added with keeping the temperature thereof, and was stirred at a temperature of 5° C. or less for 2 hours. This was poured into 1400 g of ice/600 ml of water while being stirred at a temperature of 10° C. or less to be further dispersed for 1 hour after the pouring was completed. After standing, the supernatant was removed and filtered. After being washed with 2000 ml of water, the cake was dispersed into 1800 ml of water and suction-filtered. The cake was washed with 800 ml of water. The water-washed cake was added to 550 ml of hot water and 66 ml of 25%-aqueous ammonia to be dispersed under reflux for 6 hours. After being filtered, the cake was washed with 600 ml of hot water (60° C.) and 1650 ml of ion exchange water (IEW). When pH and conductivity of the filtrate are an equal level to those of the ion exchange water, the cake was dried at a temperature of 70° C. to obtain 13.24 g of blue solid.

Then, 9.0 g of the obtained blue solid and 150 ml of o-dichlorobenzene were charged into a 300-ml flask and were stirred at a temperature of 170 to 180° C. This mixture was refluxed and stirred for 10 hours with removing water to be produced. After being filtered under heating at a temperature of 130° C., the obtained wet cake was sprinkled and washed sequentially with 225 ml of hot DMF (110° C.), 45 ml of DMF, 90 ml of methanol and 225 ml of IEW, thereafter the obtained cake was dried at a temperature of 70° C. to obtain 7.62 g of a polymorph including a μ-oxo aluminum/gallium naphthalocyanine dimer NcAl—O—GaNc in a form of mixed crystal.

It was confirmed through the results of mass spectrum of this compound by TOF-MS (time-of-flight mass spectrum) that the compound was a mixture of a μ-oxo aluminum/gallium naphthalocyanine dimer, a μ-oxo aluminum naphthalocyanine dimer and a μ-oxo gallium naphthalocyanine dimer.

Comparative Example 2

A sample was made by simply mixing titanyl naphthalocyanine (O=TiNc) obtained in Synthesis Example 1 and chlorogallium naphthalocyanine (ClGaNc) obtained in Synthesis Example 5 by equivalent moles to each other.

Figure 10:
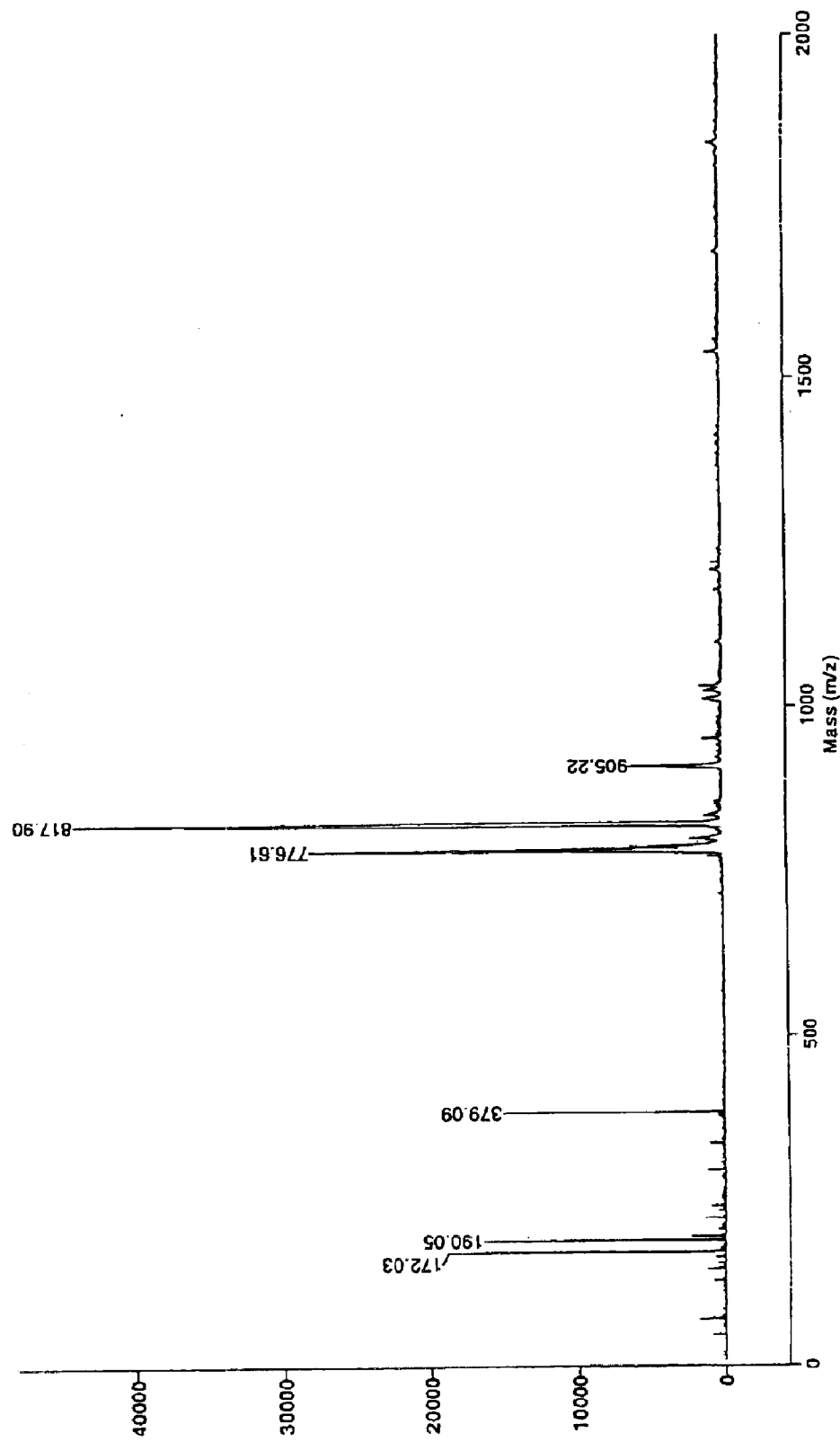
FIG. 10 is a TOF-MS spectrum of Comparative Example 2.

A mass spectrum of this simple mixture by TOF-MS is shown in FIG. 10.

Comparative Example 3

A sample was made by simply mixing titanyl naphthalocyanine obtained in Synthesis Example 1 and chlorogallium phthalocyanine obtained in Synthesis Example 5 by equivalent moles to each other.

Comparative Example 4

A sample was made by simply mixing titanyl phthalocyanine obtained in Synthesis Example 2 and chlorogallium naphthalocyanine obtained in Synthesis Example 6 by equivalent moles to each other.

Figure 11:
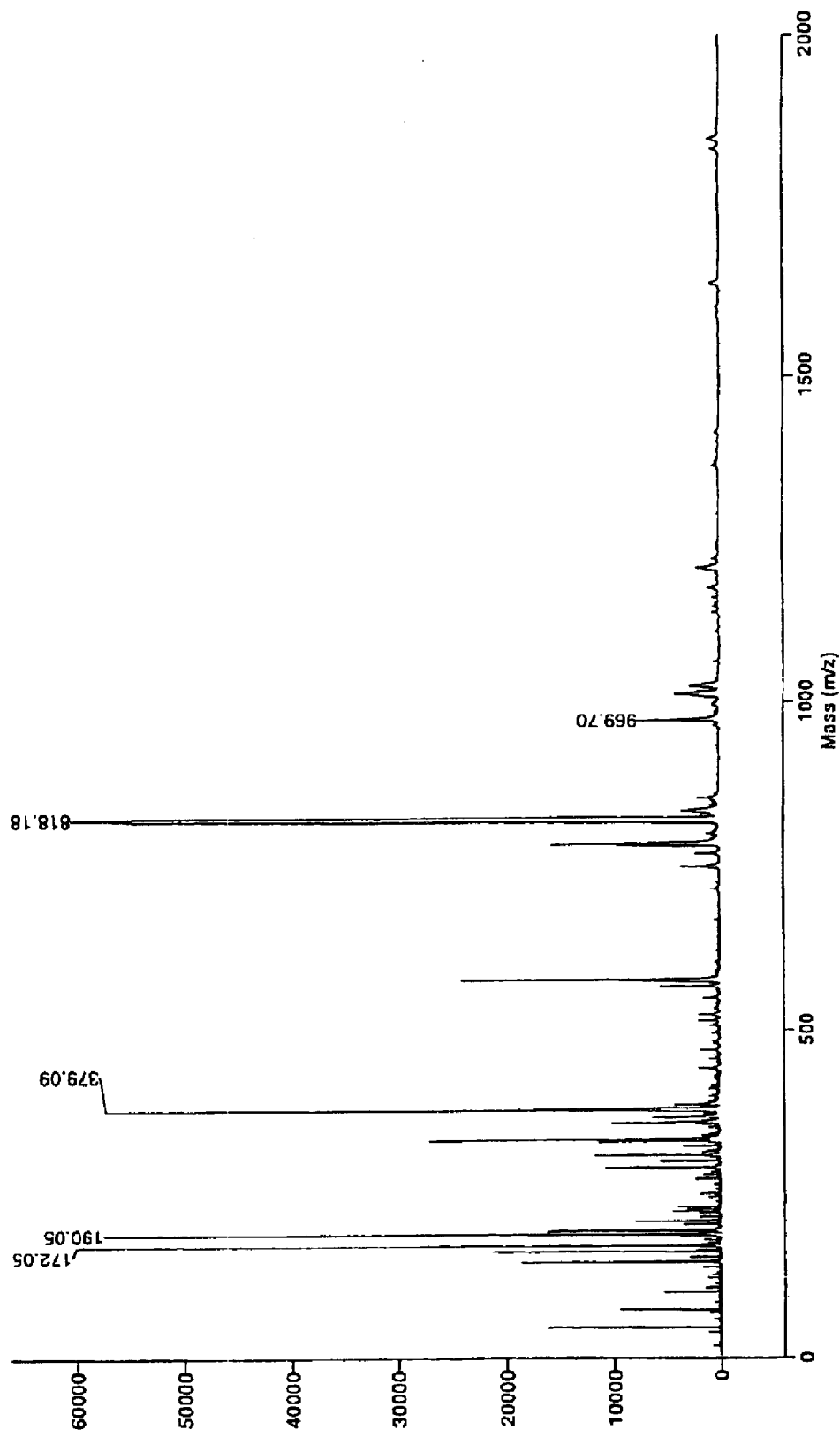
FIG. 11 is a TOF-MS spectrum of Comparative Example 4.

A mass spectrum of this simple mixture by MALDI-TOFMS is shown in FIG. 11.

The results of mass spectrum by TOF-MS are shown in Tables 9 and 10, with reference to each of the compounds in Examples 1, 2, 3, 7 and 8 as well as the simply mixed samples in Comparative Examples 2 and 4.

TABLE 9

Figure 4:
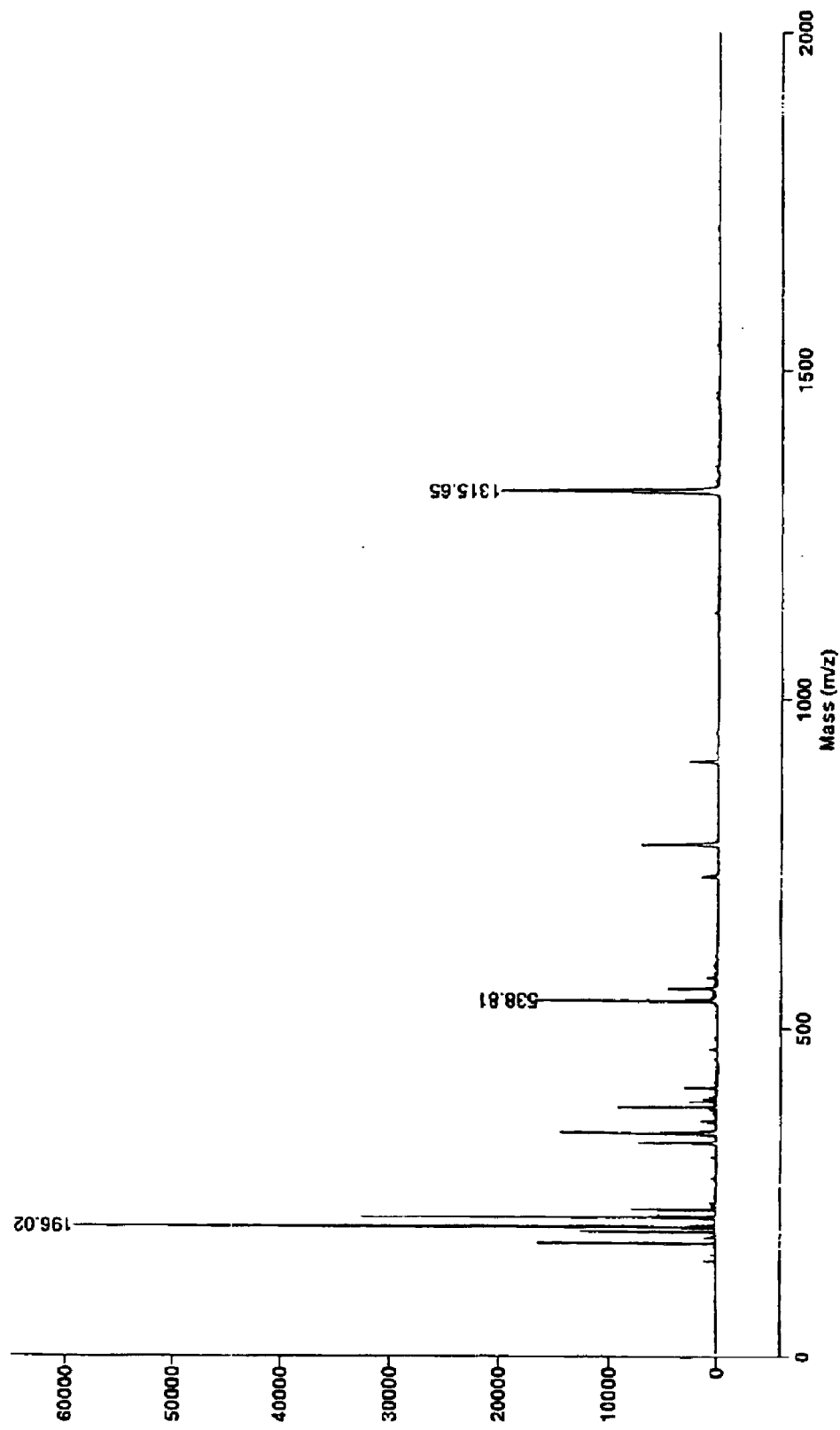
FIG. 4 is a TOF-MS spectrum of Example 7.

| Example No. | Ratio | ClM1Nc (Pc) | O=M2Nc (Pc) | Condition | TOF-MS (FIG #) |
|---|---|---|---|---|---|
| Example 1 | 1:1 | ClGaNc | O=TiNc | Described in Example 1 | $M^+$(1559, selective) GaNc(l) (FIG. 1) |
| Example 2 | 1:1 | ClGaNc | O=TiPc | Described in Example 2 | $M^+$(1359, selective) GaNc(m), —O—TiPc(m) (FIG. 2) |
| Example 3 | 1:1 | ClGaPc | O=TiNc | Described in Example 3 | $M^+$(1359, selective) GaPc(l), —O—TiNc(m) (FIG. 3) |
| Example 4 | 1:1 | ClGaNc | O=VNc | Described in Example 4 | $M^+$(1562, selective) GaNc(l), —O—VNc(l) |
| Example 5 | 1:1 | ClGaPc | O=VNc | Described in Example 5 | $M^+$(1362, selective) GaPc(l), —O—VNc(l) |
| Example 6 | 1:1 | ClGaNc | O=VPc | Described in Example 6 | $M^+$(1362, selective) GaNc(l), —O—VPc(l) |
| Example 7 | 1:1 | ClAlPc | O=TiNc | Described in Example 7 | $M^+$(1316, selective) (FIG. 4) |
| Example 8 | 1:1 | ClGaPc(t-Bu)$_4$ | O=TiNc | Described in Example 8 | $M^+$(1583, selective) (t-Bu)$_4$PcGa(m), —O—TiNc(s) (FIG. 5) |

TABLE 10

| Example No. | Ratio | ClM1Nc (Pc) | O=M2Nc (Pc) | Condition | TOF-MS (FIG #) |
|---|---|---|---|---|---|
| Comparative Example 1 | 1:1 | ClGaNc ClAlNc | — | Sulfuric acid treatment Drying Dehydration | $M^+$(1137) (NcAl)$_2$O (NcGA)$_2$O |
| Comparative Example 2 | 1:1 | ClGaNc | O=TiNc | Simple mixing | $M^+$(1559) None O=TiNc (PP selective) ClGaNc (PP selective) (FIG. 10) |
| Comparative Example 3 | 1:1 | ClGaPc | O=TiNc | Simple mixing | $M^+$(1359) None O=TiNc (PP selective) ClGaPc (PP selective) |
| Comparative Example 4 | 1:1 | ClGaNc | O=TiPc | Simple mixing | $M^+$(1359) None O=TiPc (PP selective) ClGaNc (PP selective) (FIG. 11) |

Each abbreviation in Tables 9 and 10 is as follows.

Ratio represents the reaction molar ratio or the mixture ratio (molar ratio) of halometallo-naphthalocyanine or phthalocyanine to oxymetallo-naphthalocyanine or phthalocyanine.

ClGaNc: chlorogallium naphthalocyanine
ClGaPc: chlorogallium phthalocyanine
ClAlNc: chlorogallium naphthalocyanine
ClAlPc: chlorogallium phthalocyanine
GaNc: a fraction of the corresponding dimer
GaPc: a fraction of the corresponding dimer
O=TiNc: titanyl naphthalocyanine
O=Pc: titanyl phthalocyanine
O=VNc: vanadyl naphthalocyanine
O=VPc: vanadyl phthalocyanine
O=TiPc(t-Bu)$_4$: tetrakis(tert-butyl)titanyl phthalocyanine
(t-Bu)$_4$PcGa: tetrakis(tert-butyl)gallium phthalocyanine
—O—TiNc: a fraction of titanyl naphthalocyanine
—O—TiPc: a fraction of titanyl phthalocyanine —O—VNc: a fraction of vanadyl naphthalocyanine —O—VPc: a fraction of vanadyl phthalocyanine (NcAl)$_2$O: a μ-oxo aluminum naphthalocyanine dimer [NcAl—O—AlNc]

(NcGa)$_2$O: a μ-oxo gallium naphthalocyanine dimer [NcGa—O—GaNc]

(l): a large peak intensity (m): a medium peak intensity (s): a small peak intensity M$^+$ in Tables 9 and 10 represents the parent peak (PP) of a μ-oxo bridged heterometal compound in TOF-MS.

What is claimed is:

1. A μ-oxo bridged heterometal naphthalo/naphthalocyanine compound represented by the following formula I:

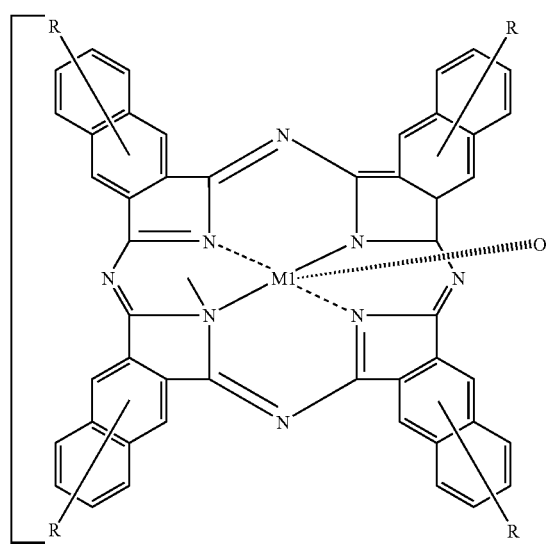

I

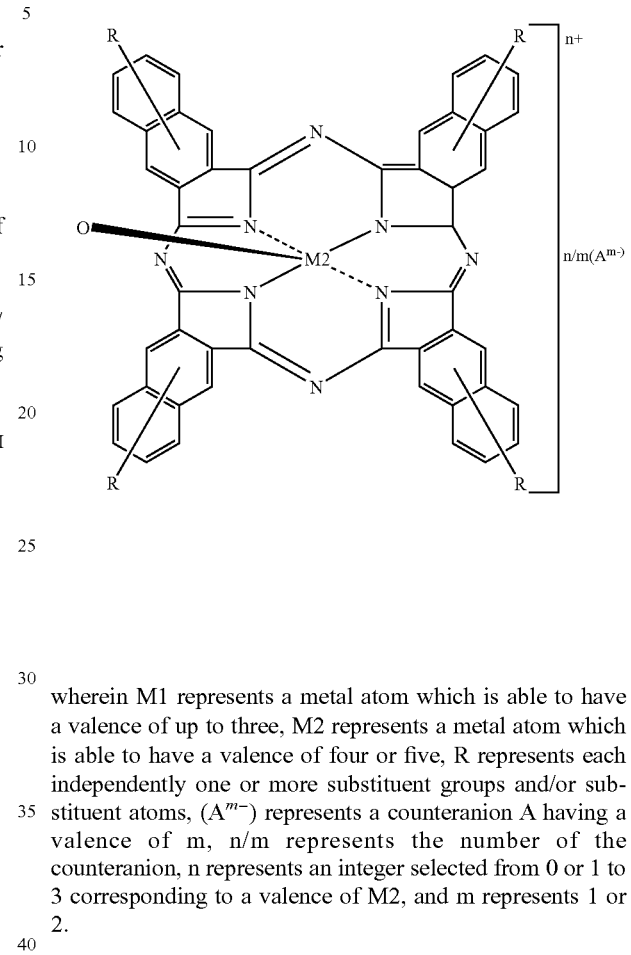

wherein M1 represents a metal atom which is able to have a valence of up to three, M2 represents a metal atom which is able to have a valence of four or five, R represents each independently one or more substituent groups and/or substituent atoms, (A$^{m-}$) represents a counteranion A having a valence of m, n/m represents the number of the counteranion, n represents an integer selected from 0 or 1 to 3 corresponding to a valence of M2, and m represents 1 or 2.

2. A μ-oxo bridged heterometal phthalo/naphthalocyanine compound represented by the following formula II:

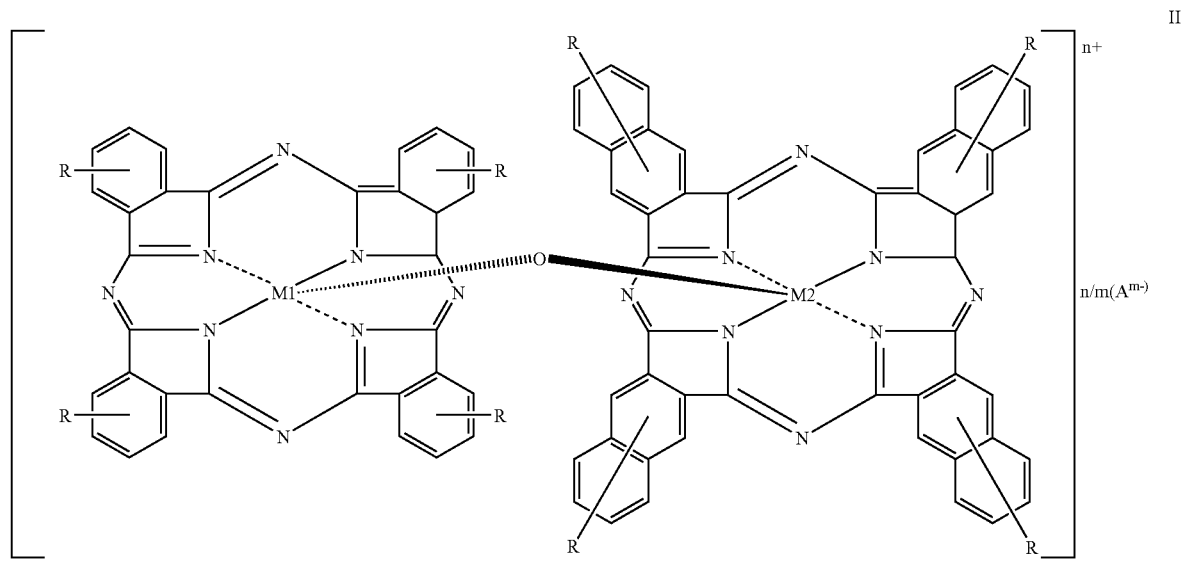

II wherein M1 represents a metal atom which is able to have a valence of up to three, M2 represents a metal atom which is able to have a valence of four or five, R represents each independently one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

3. A μ-oxo bridged heterometal naphthalo/phthalocyanine compound represented by the following formula III:

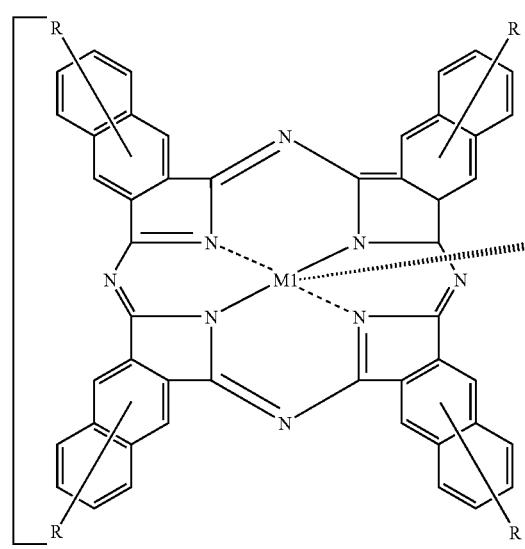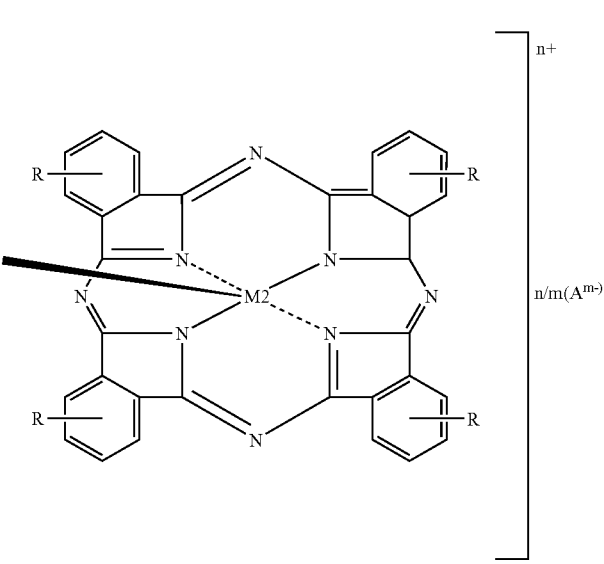

wherein M1 represents a metal atom which is able to have a valence of up to three, M2 represents a metal atom which is able to have a valence of four or five, R represents each independently one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

4. The compound according to any one of claims 1 to 3, wherein the M1 is gallium or aluminum.

5. The compound according to claim 1, wherein the M2 is titanium or vanadium.

6. A production method of the μ-oxo bridged heterometal naphthalo/naphthalocyanine compound according to claim 1, comprising the step of:
reacting naphthalocyanine having a halometal (III) as a central metal thereof with naphthalocyanine having an oxymetal (IV or V) as a central metal thereof by equivalent moles to each other.

7. A production method of the μ-oxo bridged heterometal phthalo/naphthalocyanine compound according to claim 2, comprising the step of:
reacting phthalocyanine having a halometal (III) as a central metal thereof with naphthalocyanine having an oxymetal (IV or V) as a central metal thereof by equivalent moles to each other.

8. A production method of the μ-oxo bridged heterometal naphthalo/phthalocyanine compound according to claim 3, comprising the step of:
reacting naphthalocyanine having a halometal (III) as a central metal thereof with phthalocyanine having an oxymetal (IV or V) as a central metal thereof by equivalent moles to each other.

9. The production method according to any one of claims 6 to 8, further comprising the step of:
stabilizing a reacted compound by using aqueous ammonia.

* * * * *